(12) United States Patent
Motai

(10) Patent No.: US 9,872,727 B2
(45) Date of Patent: Jan. 23, 2018

(54) ENERGY TREATMENT DEVICE

(71) Applicant: OLYMPUS CORPORATION, Tokyo (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/932,571

(22) Filed: Nov. 4, 2015

(65) Prior Publication Data

US 2016/0120595 A1 May 5, 2016

Related U.S. Application Data

(63) Continuation of application No. PCT/JP2014/077064, filed on Oct. 9, 2014.
(Continued)

(51) Int. Cl.
*A61B 18/14* (2006.01)
*A61B 17/29* (2006.01)
(Continued)

(52) U.S. Cl.
CPC .......... *A61B 18/1447* (2013.01); *A61B 18/14* (2013.01); *A61B 18/1482* (2013.01);
(Continued)

(58) Field of Classification Search
CPC ............ A61B 18/14; A61B 2018/1452; A61B 2018/144; A61B 2018/141;
(Continued)

(56) References Cited

U.S. PATENT DOCUMENTS

| 2002/0068951 | A1 | 6/2002 | Burbank et al. |
| 2006/0064113 | A1 | 3/2006 | Nakao |
| 2008/0015409 | A1* | 1/2008 | Barlow ............... A61B 18/1492 600/106 |

FOREIGN PATENT DOCUMENTS

| EP | 1281360 A1 | 2/2003 |
| JP | H09-56719 A | 3/1997 |

(Continued)

OTHER PUBLICATIONS

Jan. 13, 2015 International Search Report issued in International Patent Application No. PCT/JP2014/077064.
(Continued)

*Primary Examiner* — Jaymi Della
(74) *Attorney, Agent, or Firm* — Oliff PLC

(57) ABSTRACT

The present energy treatment device has an insertion part, a pair of arms which are provided in a distal portion of the insertion part and which are capable of performing an opening-closing operation, a treatment member which is attachably and detachably provided in a first arm, a locked part which is provided in a second arm and which is capable of locking the treatment member, and a manipulation part which causes the pair of arms to perform an opening-closing operation, wherein the treatment member includes a knife wire, and a locking member which is positioned with respect to the first arm, being attachable to and detachable from the first arm, and capable of being locked by the locked part, the locked part has a retainer which is capable of holding the locking member with a force stronger than a force of the first arm to hold the locking member.

6 Claims, 15 Drawing Sheets

Related U.S. Application Data

(60) Provisional application No. 61/891,057, filed on Oct. 15, 2013.

(51) Int. Cl.
    *A61B 17/42*      (2006.01)
    *A61B 18/00*      (2006.01)

(52) U.S. Cl.
    CPC ... *A61B 18/1445* (2013.01); *A61B 2017/2926* (2013.01); *A61B 2017/2945* (2013.01); *A61B 2017/4216* (2013.01); *A61B 2018/00178* (2013.01); *A61B 2018/00559* (2013.01); *A61B 2018/00601* (2013.01); *A61B 2018/141* (2013.01); *A61B 2018/144* (2013.01); *A61B 2018/1452* (2013.01)

(58) Field of Classification Search
    CPC .......... A61B 2018/00601; A61B 2018/00559; A61B 2018/00178; A61B 2017/4216; A61B 2017/2945; A61B 2017/2926; A61B 18/1482; A61B 18/1447; A61B 18/1445

See application file for complete search history.

(56) References Cited

FOREIGN PATENT DOCUMENTS

| | | |
|---|---|---|
| JP | H10-234743 A | 9/1998 |
| JP | 2010-178766 A | 8/2010 |
| WO | 2007/102586 A1 | 9/2007 |

OTHER PUBLICATIONS

Jun. 23, 2017 Search Report issued in European Patent Application No. 14854818.3.

\* cited by examiner

ENERGY TREATMENT DEVICE

This application is a continuation application based on a PCT International Application No. PCT/JP2014/077064, filed on Oct. 9, 2014, whose priority is claimed on U.S. provisional Patent Application No. 61/891,057, filed on Oct. 15, 2013. The contents of the PCT International Application and the United States provisional Patent Application are incorporated herein by reference.

TECHNICAL FIELD

The present invention relates to an energy treatment device.

BACKGROUND ART

Medical devices for performing surgical operations through an endoscope are known. For example, Japanese Unexamined Patent Application, First Publication No. H10-234743A discloses a high-frequency excision tool which can be combined with an endoscope. In addition, Japanese Unexamined Patent Application, First Publication No. 2010-178766A discloses an endoscope for treatment which can be combined with a high-frequency snare device which incises tissues by applying a high-frequency current thereto. The endoscope for treatment disclosed in Japanese Unexamined Patent Application, First Publication No. 2010-178766A has an engaging part to which the loop portion of the high-frequency snare device can be caught at a distal end, and is configured to excise entire layers of a wall of a body object using a wire portion of the high-frequency snare device positioned at more proximal than the loop portion as an incision electrode.

SUMMARY OF INVENTION

According to an energy treatment device of a first aspect of the present invention, the energy treatment includes an insertion part which is capable of being inserted into a body, a pair of arms which has a first arm and a second arm, the first arm and the second arm being provided in a distal portion of the insertion part and being capable of performing an opening-closing operation, a treatment member which is attachably and detachably provided in the first arm and which performs treatment on a treatment target site, a locked part which is provided in the second arm and which is capable of locking the treatment member, and a manipulation part which causes the pair of arms to perform an opening-closing operation. The treatment member includes a knife wire configured to have conductivity and to incise a biological tissue using electrical energy, and a locking member which is positioned with respect to the first arm, being attachable to and detachable from the first arm and capable of being locked by the locked part. The locked part has a retainer which is capable of holding the locking member with a force stronger than a force of the first arm to hold the locking member. The insertion part has a shaft to which each of the first arm and the second arm is connected so as to be swingable about a same or parallel axis lines respectively. The first arm includes a first proximal arm which is coupled to a distal end part of the shaft and which swings with respect to the shaft between a state in which the first proximal arm extends in parallel with a longitudinal axis of the shaft and a state in which the first proximal arm inclines to the longitudinal axis and extends toward a radially outward of the shaft, and a first distal arm which is coupled to the first proximal arm and which swings with respect to the first proximal arm between a state in which the first distal arm extends in a direction in which the first proximal arm extends and a state in which the first distal arm inclines to the direction in which the first proximal arm extends. After the first arm and the second arm are moved to a position in which the first arm and the second arm are in proximity to each other by the opening-closing operation, the locking member held by the first arm is held by the retainer, and the locking member detaches from the first arm while the locking member is held by the retainer of the second arm through an operation in which the first arm and the second arm are separated from each other.

According to a second aspect of the present invention based on the first aspect, the second arm may include a second proximal arm which is coupled to the distal end part of the shaft and which swings with respect to the shaft between a state in which the second proximal arm extends in parallel with the longitudinal axis of the shaft and a state in which the second proximal arm inclines to the longitudinal axis and extends toward a radially outward of the shaft, and a second distal arm which is coupled to the second proximal arm and which swings with respect to the second proximal arm between a state in which the second distal arm extends in a direction in which the second proximal arm extends and a state in which the second distal arm inclines to the direction in which the first proximal arm extends.

According to a third aspect of the present invention based on the second aspect, the manipulation part may include a first stopper mechanism which maintains a bending state of the first distal arm with respect to the first proximal arm, a second stopper mechanism which maintains a bending state of the second distal arm with respect to the second proximal arm, and an opening-closing manipulation mechanism for causing the pair of arms to perform an opening-closing operation by causing the first proximal arm and the second proximal arm to swing with respect to the shaft while maintaining a state in which the first proximal arm and the second proximal arm have an equal inclination angle with respect to the longitudinal axis of the shaft.

According to a fourth aspect of the present invention based on the third aspect, the second arm may include a guide part into which the locking member is capable of being inserted and which has a slit part that serves as the retainer, and an engaging part which is disposed on a distal side of the guide part, communicating with the guide part, and being capable of engaging with the locking member. When the first arm moves the locking member to a distal side of the second arm from the guide part, the locking member may engage with the engaging part.

According to a fifth aspect of the present invention based on the fourth aspect, the locking member may have conductivity and may be electrically and mechanically connected to the knife wire. The engaging part may have a contact point part that is electrically connected with the locking member when the locking member engages with the engaging part. The manipulation part may include a connector which is capable of being connected to a high-frequency power supply device, the high-frequency power supply device that is capable of supplying a high-frequency current, a first connection part which electrically connects the connector and the knife wire, and a second connection part which electrically connects the connector and the contact point part. The high-frequency current supplied via the connector may be applied to the knife wire when the contact point part is electrically connected with the locking member in the engaging part.

According to a sixth aspect of the present invention based on the second aspect, at least one of the first distal arm and the second distal arm may be configured to perform a curving operation.

DESCRIPTION OF EMBODIMENTS

Figure 1:
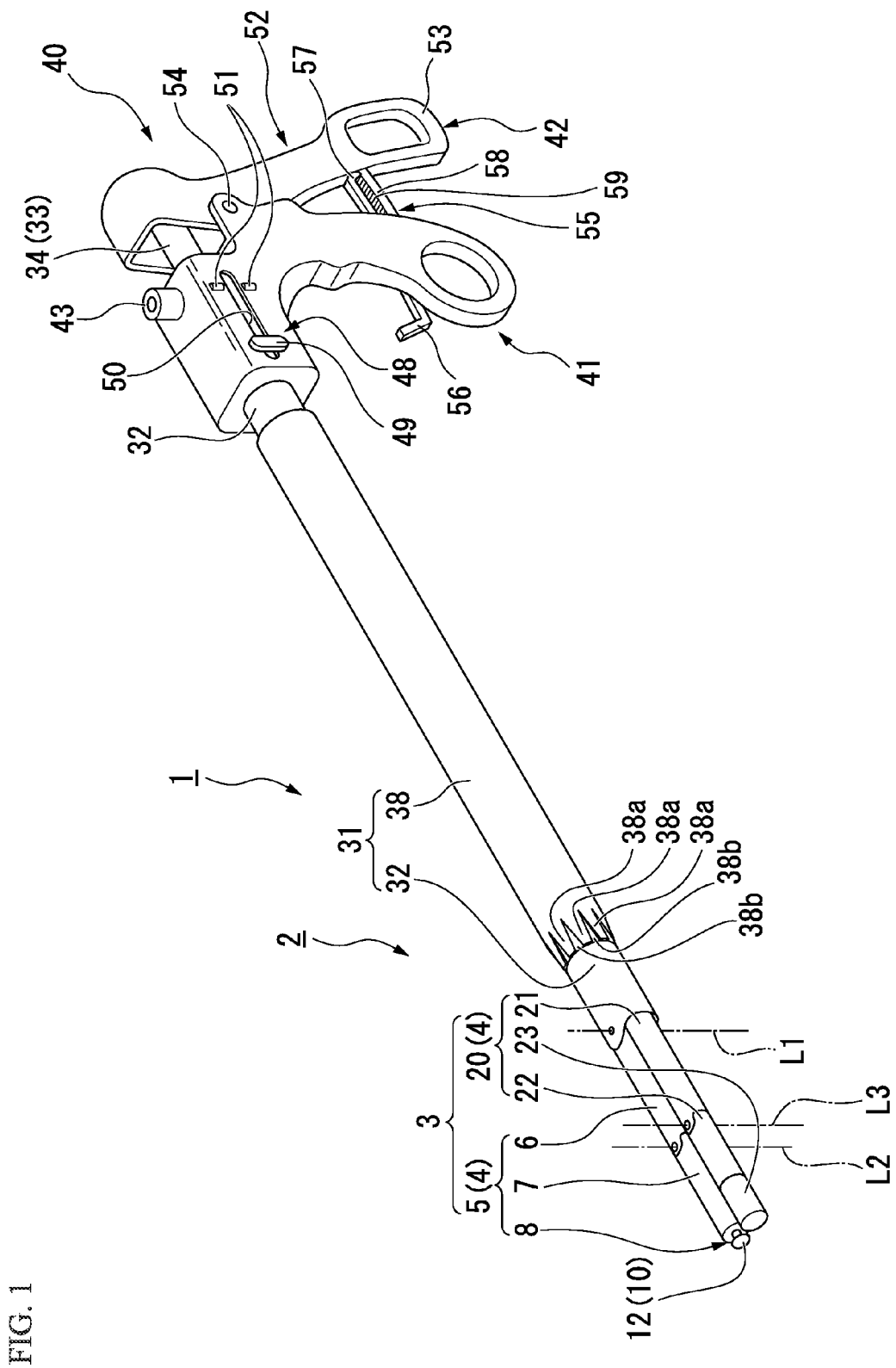
FIG. 1 is a perspective view of an energy treatment device according to an embodiment of the present invention.
Figure 2:
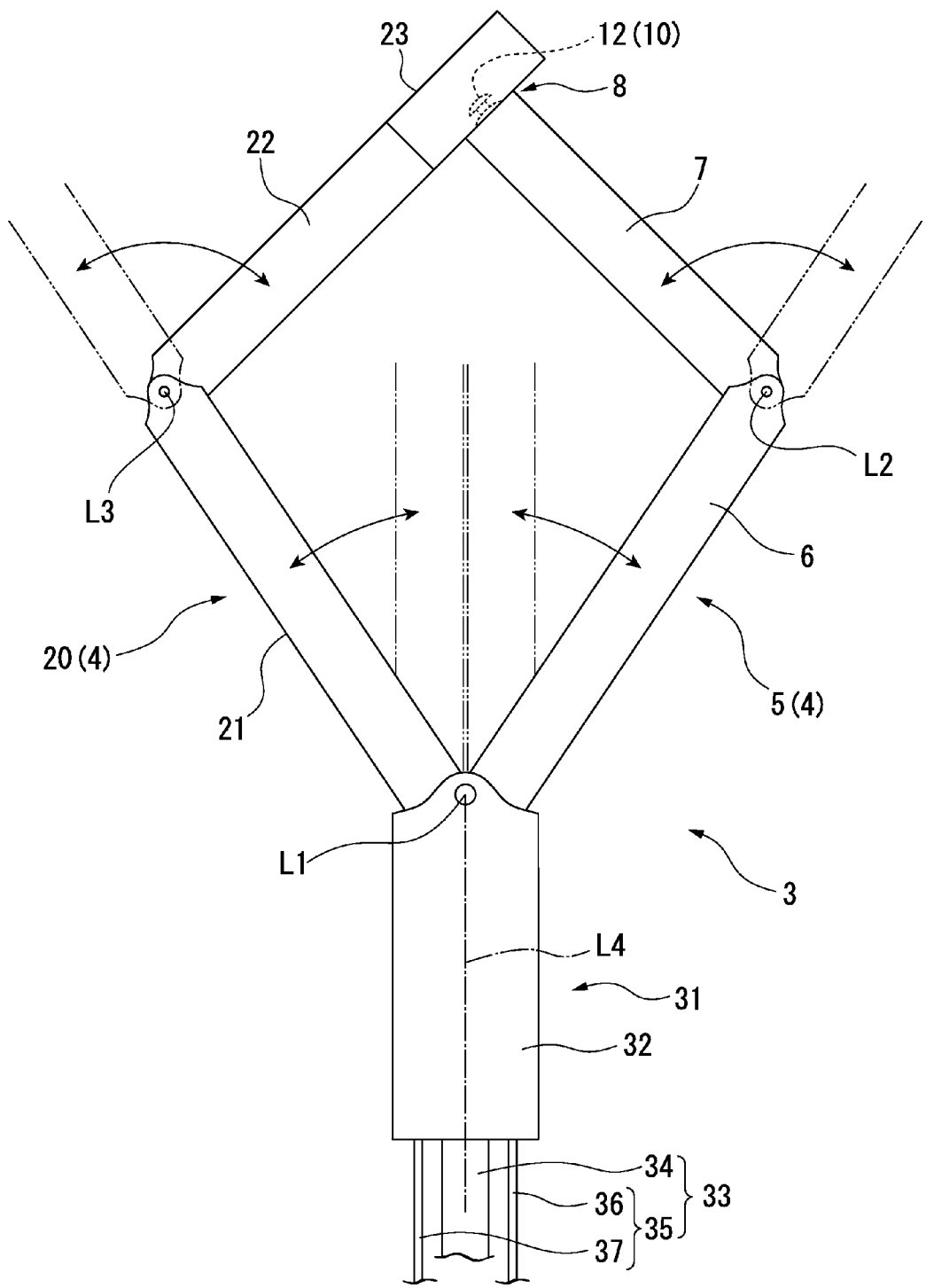
FIG. 2 is a plan view showing a distal portion of the energy treatment device according to the embodiment of the present invention.

An energy treatment device according to an embodiment of the present invention will be described. FIG. 1 is a perspective view of the energy treatment device 1 according to the embodiment of the present invention. FIG. 2 is a plan view showing a distal portion of the energy treatment device 1. The energy treatment device 1 according to the present embodiment is a medical device which can incise tissues by applying a high-frequency current thereto. The energy treatment device 1 according to the present embodiment shown in FIG. 1 is used to incise tissues. Specifically, the energy treatment device 1 according to the present embodiment is suitable for incising a tissue having a shape or dimensions which make the tissue difficult to be incised using the loop portion of a known high-frequency snare device.

As shown in FIGS. 1 and 2, the energy treatment device 1 has an insertion part 2, a manipulation part 40, and a transmission part 33. The insertion part 2 has a distal end and a proximal end, and is configured to be inserted into a body. The manipulation part 40 is connected with the proximal end of the insertion part 2. The transmission part 33 is disposed inside the insertion part 2 and the manipulation part 40.

The insertion part 2 has a distal constitution part 3 and a pipe part 31. The distal constitution part 3 is provided to perform treatment on a treatment target site. The pipe part 31 is coupled to a proximal portion of the distal constitution part 3.

As shown in FIG. 2, the distal constitution part 3 has a pair of arms 4 (a first arm 5 and a second arm 20). The pair of arms 4 are coupled to a distal end of the pipe part 31. At least the outer surfaces of the pair of arms 4 have an insulating property. For example, the pair of arms 4 may be covered by an insulating material.

The first arm 5 has a first proximal arm 6, a first distal arm 7, and a first treatment part 8. The first proximal arm 6 is coupled to the distal end of the pipe part 31. The first distal arm 7 is coupled to a distal end of the first proximal arm 6. The first treatment part 8 is disposed at a distal end of the first distal arm 7.

The first proximal arm 6 is a tubular member with a distal end and a proximal end. The proximal end of the first proximal arm 6 and the distal end of the pipe part 31 are coupled with each other such that the arms can swing on a swing axis line L1. In the present embodiment, the swing axis line L1 is orthogonal to the longitudinal axis L4 of the pipe part 31. The first proximal arm 6 can swing with respect to the pipe part 31 through a manipulation of the manipulation part 40.

The first distal arm 7 is a tubular member with a distal end and a proximal end. The proximal end of the first distal arm 7 and the distal end of the first proximal arm 6 are coupled with each other such that the arms can swing on a swing axis line L2. The swing axis line L2 is orthogonal to a longitudinal axis of the first proximal arm 6. In addition, the swing axis line L2 is parallel with another swing axis line L3 between a second proximal arm 21 and a second distal arm 22 to be described below. In the present embodiment, the swing axis line L2 between the proximal end of the first distal arm 7 and the distal end of the first proximal arm 6 is orthogonal to the longitudinal axis of the first proximal arm 6. Further, in the present embodiment, the swing axis line L2 between the proximal end of the first distal arm 7 and the distal end of the first proximal arm 6 is parallel with the swing axis line L1 between the first proximal arm 6 and the pipe part 31. The first distal arm 7 can swing with respect to the first proximal arm 6 through a manipulation of the manipulation part 40.

Figure 3:
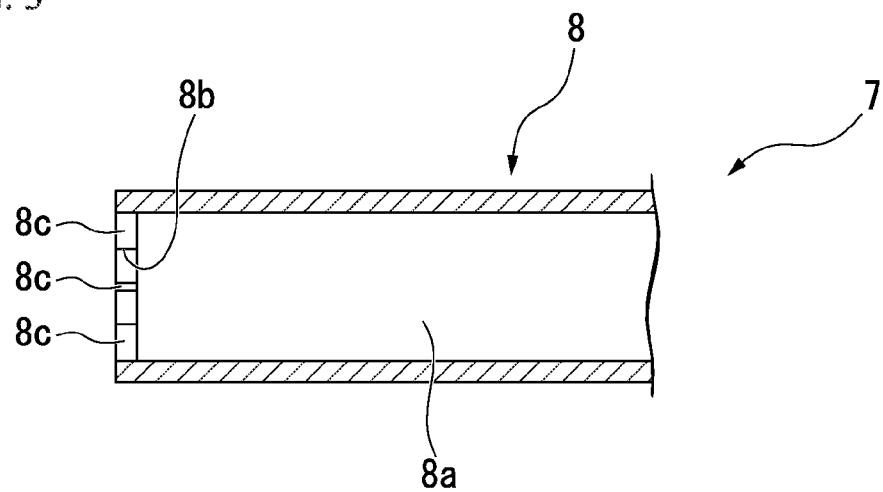
FIG. 3 is a cross-sectional view showing an inner structure of a first treatment part of the energy treatment device according to the embodiment of the present invention.
Figure 4:
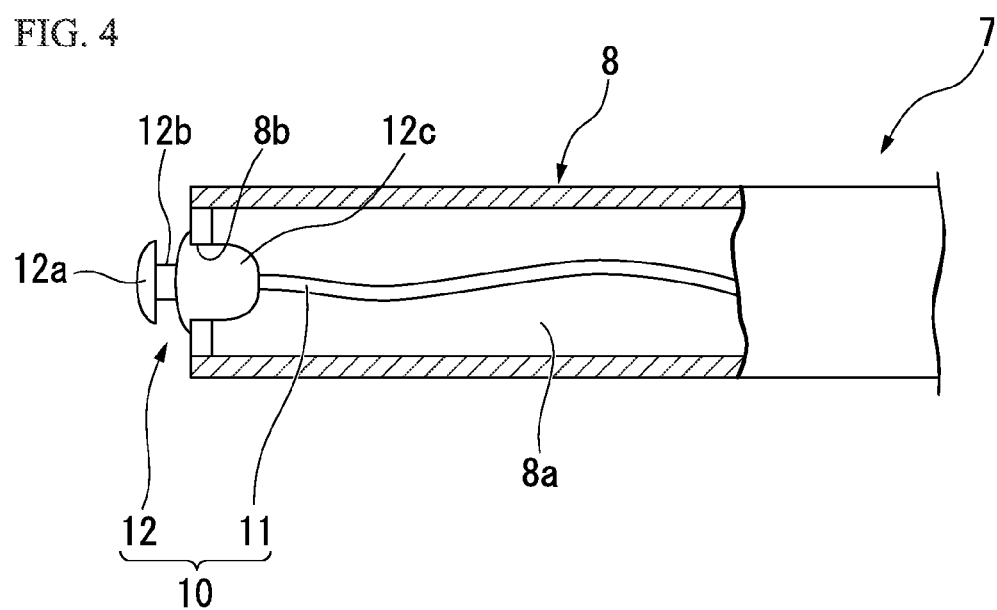
FIG. 4 is a partial cross-sectional view showing a state in which a treatment member is installed in the first treatment part of the energy treatment device according to the embodiment of the present invention.

FIG. 3 is a cross-sectional view showing an inner structure of a first treatment part 8 of the energy treatment device 1 according to the present embodiment. FIG. 4 is a partial cross-sectional view showing a state in which a treatment member 10 is installed in the first treatment part 8 of the present embodiment.

As shown in FIGS. 2 and 3, the first treatment part 8 is fixed to the distal end of the first distal arm 7. As shown in FIG. 4, the first treatment part 8 is coupled to the treatment member 10 which is for treating a treatment target site. The first treatment part 8 can hold the treatment member 10 in states in which the treatment member 10 projects along the longitudinal axis of the first distal arm 7 and toward a further distal side from the distal end of the first distal arm 7. The treatment member 10 has a knife wire 11 and a locking member 12. The knife wire 11 is configured to incise a biological tissue by applying a high-frequency current to the biological tissue. The locking member 12 is fixed to a distal end of the knife wire 11.

As shown in FIG. 3, a cavity 8a is formed inside the first treatment part 8. The knife wire 11 is inserted into the cavity 8a so that the knife wire can be advanced from and retracted into the cavity. The cavity 8a formed in the first treatment part 8 communicates with the inside of the first distal arm 7. The cavity 8a formed in the first treatment part 8 is open at the distal end of the first treatment part 8, and the locking member 12 is locked in an opening 8b formed at the distal end of the first treatment part 8. The opening 8b can be flexibly deformed, and the locking member 12 can be fixed to the opening 8b. Furthermore, a slit 8c which extends in the radial direction of the first treatment part 8 is formed in the opening 8b with a configuration in which the locking member 12 easily presses and widens the opening 8b.

As shown in FIG. 4, in a state in which the locking member 12 is locked in the opening 8b of the first treatment part 8, only a part of the locking member 12 is held in a position in which the part enters the cavity 8a when the locking member 12 comes in contact with a distal end face of the first treatment part 8, and thus the locking member 12 is locked in the opening 8b due to frictional force. Then, when the locking member 12 is pulled out from the opening of the first treatment part 8 with a force greater than the frictional force exerted between the opening 8b of the first treatment part 8 and the locking member 12, the locking member 12 is withdrawn from the first treatment part 8. As described above, the locking member 12 of the treatment member 10 can be attached to and detached from the first arm 5.

The knife wire 11 extends from the opening of the first treatment part 8 to the manipulation part 40 through the inside of the cavity 8a of the first treatment part 8, the inside of the first distal arm 7, the inside of the first proximal arm 6, and the inside of the pipe part 31. A proximal end (first connection part) of the knife wire 11 is connected to a connector 43 (see FIG. 1) to be described below. The proximal end of the knife wire 11 receives supply of a high-frequency current from a high-frequency power supply device via the connector 43.

The knife wire 11 shown in FIG. 4 is disposed from the cavity 8a of the first treatment part 8 to the manipulation part 40 (see FIG. 1) to have a certain degree of slack with respect to the first treatment part 8, the first arm 5, and the pipe part 31. Accordingly, the knife wire 11 is configured such that, when the energy treatment device 1 is used, a length of the knife wire 11 can be drawn from the opening at the distal end of the first treatment part 8 which is substantially the same as a length needed for the knife wire 11 to be wound around the outer circumference of a treatment target site. Note that an intermediate portion of the knife wire 11 or a part of a proximal end portion thereof is temporarily fixed to the first arm 5, the pipe part 31, or the manipulation part 40. For this reason, a force exerted when the knife wire 11 is drawn from the distal end of the first treatment part 8 is prevented from being transmitted directly to the connector 43. In addition, an excessive force exerted when a tissue is bound using the knife wire 11 is prevented from being transmitted to the connector 43, and poor connection or disconnection between the knife wire 11 and the connector 43 can be prevented.

As shown in FIG. 4, the locking member 12 has a large-diameter part 12a, a small-diameter part 12b, and a stopper 12c. The large-diameter part 12a has a larger size than the diameter of the knife wire 11, and is formed at the distal end thereof. The small-diameter part 12b has a smaller diameter than the large-diameter part 12a and is formed on a proximal side of the large-diameter part 12a. The stopper 12c has a larger diameter than the small-diameter part 12b, and is formed on a proximal side of the small-diameter part 12b. The large-diameter part 12a is larger than the minimum value of a space of a second slit part 271 that will be described below. The small-diameter part 12b is smaller than the minimum value of the space of the second slit part 271. The stopper 12c is larger than the internal dimensions of the opening 8b at the distal end of the first treatment part 8.

The locking member 12 of the present embodiment is a conductor which is electrically connected to the knife wire 11. A material of the locking member 12 is not particularly limited as long as the material is a conductor. For example, stainless steel is a suitable material for the locking member 12. The locking member 12 is fixed to the distal end of the knife wire 11 using a method such as welding or caulking. The locking member 12 may be formed to be integrated with the knife wire 11.

As shown in FIG. 2, the second arm 20 has a second proximal arm 21, a second distal arm 22, and a second treatment part 23. The second proximal arm 21 is coupled to the distal end of the pipe part 31. The second distal arm 22 is coupled to a distal end of the second proximal arm 21. The second treatment part 23 is disposed at a distal end of the second distal arm 22.

The second proximal arm 21 is a tubular member with the distal end and a proximal end. The proximal end of the second proximal arm 21 and the distal end of the pipe part 31 are coupled with each other such that the arm can swing on the swing axis line L1. The swing axis line L1 between the first proximal arm 6 and the pipe part 31 and the swing axis line L1 between the second proximal arm 21 and the pipe part 31 are the same axis. In the present embodiment, the swing axis line L1 on which the second proximal arm 21 can swing with respect to the pipe part 31 is orthogonal to the longitudinal axis of the pipe part 31.

The second proximal arm 21 can swing with respect to the pipe part 31 through a manipulation of the manipulation part 40 shown in FIG. 1. In addition, a swing operation of the second proximal arm 21 with respect to the pipe part 31 is interlinked with a swing operation of the first proximal arm 6 with respect to the pipe part 31. In the present embodiment, the first proximal arm 6 and the second proximal arm 21 are interlinked with each other to have three-dimensional rotation symmetry with the longitudinal axis L4 (see FIG. 2) of the pipe part 31 as the axis of symmetry. Furthermore, the first proximal arm 6 and the second proximal arm 21 can perform opening-closing operations with respect to the pipe part 31 so that the arms have plane symmetry with the plane which includes the longitudinal axis L4 of the pipe part 31 and extends in the direction of the swing axis line L1 of the first proximal arm 6 and the second proximal arm 21 as a plane of symmetry.

As shown in FIG. 2, the second distal arm 22 is a tubular member with the distal end and a proximal end. The proximal end of the second distal arm 22 and the distal end of the second proximal arm 21 are coupled with each other such that the arms can swing on a swing axis line L3. The swing axis line L3 is orthogonal to a longitudinal axis of the second proximal arm 21. In the present embodiment, the swing axis line L3 between the proximal end of the second distal arm 22 and the distal end of the second proximal arm 21 is a straight line orthogonal to the longitudinal axis of the second proximal arm 21. Furthermore, in the present embodiment, the swing axis line L3 between the proximal end of the second distal arm 22 and the distal end of the second proximal arm 21 is parallel with the swing axis line L1 between the second proximal arm 21 and the pipe part 31. In the present embodiment, the swing axis line L3 between the second distal arm 22 and the second proximal arm 21 is parallel with the swing axis line L2 between the first distal arm 7 and the first proximal arm 6. Furthermore, the first distal arm 7 and the second distal arm 22 swing on the same plane.

The second distal arm 22 can swing with respect to the second proximal arm 21 through a manipulation of the manipulation part 40. In the present embodiment, swing operations of the second distal arm 22 with respect to the second proximal arm 21 are performed independently of swing operations of the first distal arm 7 with respect to the first proximal arm 6.

Figure 5:
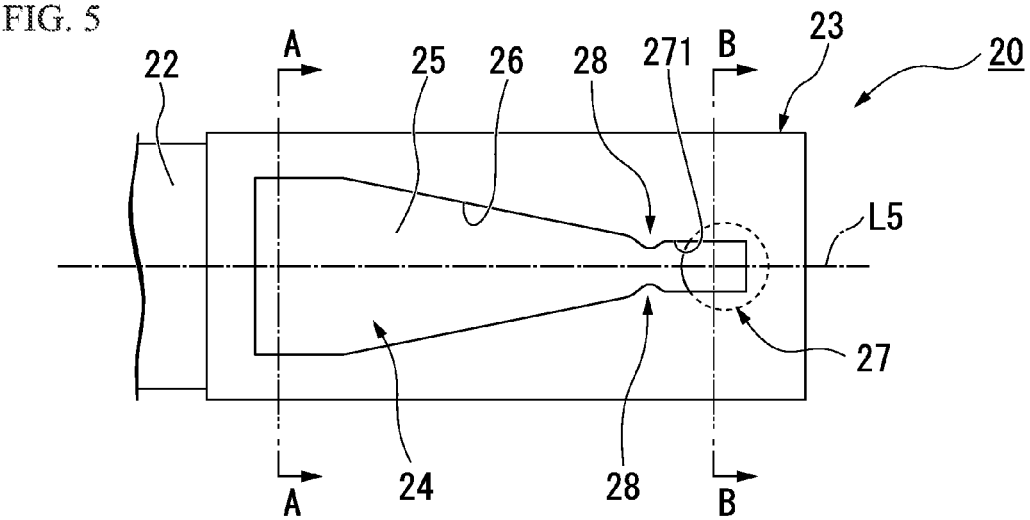
FIG. 5 is a side view showing a second treatment part of the energy treatment device according to the embodiment of the present invention.
Figure 6:
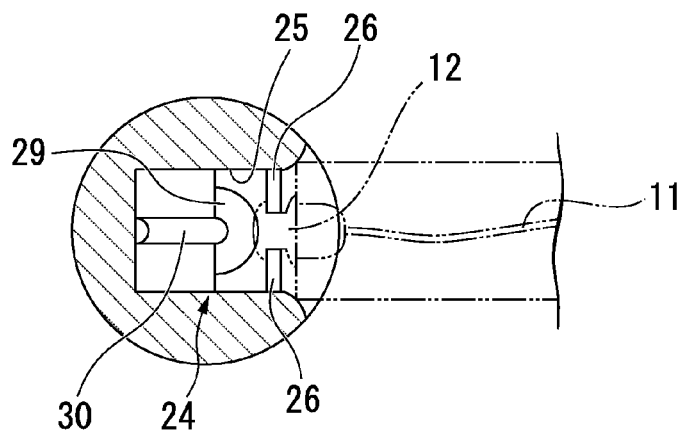
FIG. 6 is a cross-sectional view taken along the line A-A of FIG. 5.
Figure 7:
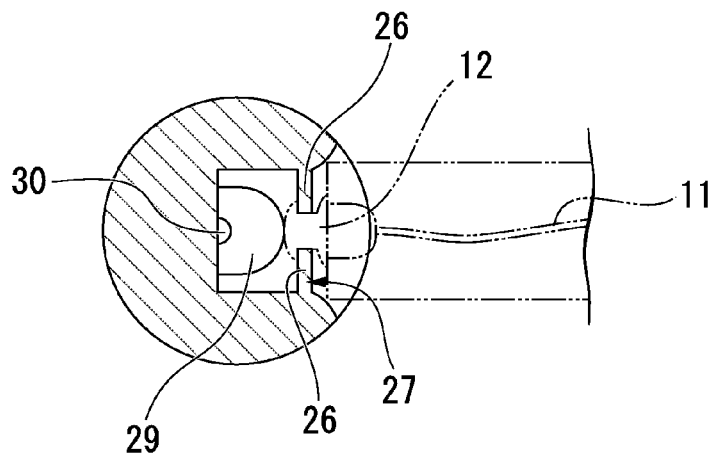
FIG. 7 is a cross-sectional view taken along the line B-B of FIG. 5.

FIG. 5 is a side view showing the second treatment part 23 of the energy treatment device 1. FIG. 6 is a cross-sectional view taken along the line A-A of FIG. 5. FIG. 7 is a cross-sectional view taken along the line B-B of FIG. 5.

As shown in FIG. 2, the second treatment part 23 is fixed to the distal end of the second distal arm 22. The second treatment part 23 protrudes from the distal end of the second distal arm 22 toward a further distal side along the longitudinal axis of the second distal arm 22.

As shown in FIG. 5, the second treatment part 23 includes a locked part 24 and an engaging part 27. The locking member 12 installed in the opening 8b of the first treatment part 8 enters the locked part 24. The engaging part 27 is configured to prevent the locking member 12 from being withdrawn from the second treatment part 23. In the second treatment part 23, the locked part 24 is disposed on a proximal side thereof, and the engaging part 27 is disposed on a distal side.

The locked part 24 has a guide part 25 and a projecting part 28. The guide part 25 has a tapered shape, and is provided to guide the locking member 12 to the engaging part 27. The projecting part 28 is a boundary portion between the locked part 24 and the engaging part 27, and is configured to prevent the locking member 12 from moving from the engaging part 27 to the locked part 24. In the present embodiment, the tapered shape of the guide part 25 is an inclined plane that expands toward an opening part.

The guide part 25 has a first slit part 26. The first slit part 26 has a width which gradually decreases toward a distal side. A portion of the first slit part 26 with a smallest opening width is the boundary between the locked part 24 and the engaging part 27, and a hole, which is very slightly smaller than the external dimensions of the small-diameter part 12b that is formed in the locking member 12, is formed therein to be opened by the projecting part 28.

As shown in FIGS. 5 and 6, the engaging part 27 has a second slit part 271 (retainer) and a contact point part 29. The second slit part 271 is formed to continue from a distal end of the first slit part 26 of the guide part 25 and the projecting part 28 and extend to the distal side. The contact point part 29 is provided to be capable of being electrically connected with the locking member 12. In the direction orthogonal to an axis line L5 of the second distal arm 22 in the plan view shown in FIG. 5, the width of the second slit part 271 of the engaging part 27 is greater than a space arranged between the projecting part 28, and the width of the second slit part 271 of the engaging part 27 is smaller than a maximum outer diameter of the locking member 12 to prevent the locking member 12 from slipping out of the second slit part 271.

In the state in which the locking member 12 is disposed at a distal end of the second slit part 271 of the engaging part 27 as shown in FIG. 7, the locking member 12 can be pulled out from the opening of the first treatment part 8 with a force greater than the frictional force exerted between the opening of the first treatment part 8 and the locking member 12.

With regard to the projecting part 28 shown in FIG. 5, when the locking member 12 moves to the distal side inside the first slit part 26 in the state in which the locking member 12 has entered the guide part 25 and further moves to the engaging part 27, the projecting part 28 comes in contact with the small-diameter part 12b formed in the locking member 12, and when the locking member 12 moves to the engaging part 27, slight resistance of the projecting part 28 against the movement of the locking member 12 occurs. For this reason, at a position of the locking member 12 moving from the guide part 25 to the engaging part 27, an operator feels an increase in resistance to his or her manipulation. In addition, the projecting part 28 prevents the small-diameter part 12b of the locking member 12 from reversely moving from the engaging part 27 to the guide part 25, and prevents the locking member 12 from slipping out from the engaging part 27 to the guide part 25 side. Accordingly, the locking member 12 of the treatment member 10 can be locked in the locked part 24. In addition, in a movement of the locking member 12 from the locked part 24 to the engaging part 27 via the projecting part 28, resistance occurring when the small-diameter part 12b formed in the locking member 12 passes the projecting part 28 is transmitted to the operator as a feeling of click. Due to the feeling of the click generated when the small-diameter part 12b formed in the locking member 12 passes the projecting part 28, the operator can discern that the locking member 12 has been guided to the engaging part 27 even in a state in which a positional relationship between the first treatment part 8 and the second treatment part 23 cannot be visually confirmed in an endoscopic image or the like.

The contact point part 29 shown in FIGS. 6 and 7 is arranged inside the engaging part 27. The contact point part 29 is a conductor which can be in contact with the locking member 12 inside the engaging part 27. The contact point part 29 has elasticity, and when the locking member 12 is positioned inside the engaging part 27, the contact point part depresses the locking member 12. The contact point part 29 has a curved surface projecting toward the first slit part 26 side. A distal end of a wire 30 (a second connection part) for supplying high-frequency current is fixed to the contact point part 29. The wire 30 extends to the connector 43 of the manipulation part 40 through the second treatment part 23, the second distal arm 22, the second proximal arm 21, and the inside of the pipe part 31. A proximal end of the wire 30 is connected with the connector 43.

As the locking member 12 is electrically connected with the contact point part 29 when the locking member 12 comes in contact with the contact point part 29 as shown in FIG. 7, high-frequency current can be applied to the knife wire 11. For this reason, in a state in which the locking member 12 is not properly engaged with the engaging part 27, an electrical connection between the locking member 12 and the contact point part 29 is insecure, and thus high-frequency current is not applied to the knife wire 11. Only in states in which the locking member 12 is properly engaged with the engaging part 27 and the locking member 12 is electrically connected with the contact point part 29, application of high-frequency current is possible.

As shown in FIG. 1, the pipe part 31 has a rigid tubular shaft 32 and a tubular outer sheath 38. The shaft 32 is coupled to the proximal end of the first proximal arm 6 and the proximal end of the second proximal arm 21. The shaft 32 is inserted into the inside of the outer sheath 38. The proximal end of the first proximal arm 6 and the proximal end of the second proximal arm 21 are coupled to a distal end of the shaft 32. A proximal end of the shaft 32 is fixed to the manipulation part 40. At least an outer surface of the pipe part 31 has an insulating property. For example, the pipe part 31 has an insulating cover part.

Figure 8:
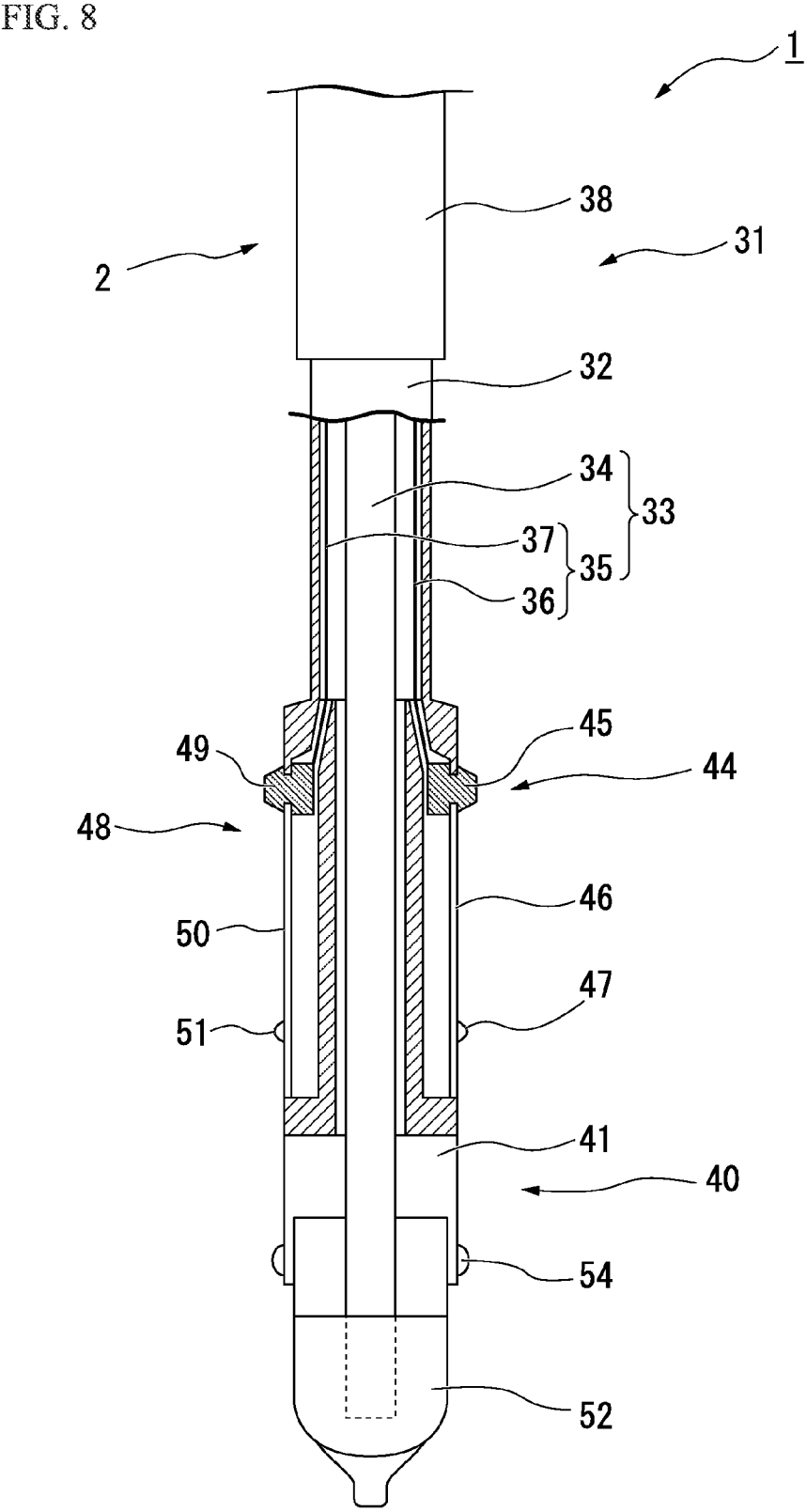
FIG. 8 is a partial cross-sectional view showing a manipulation part of the energy treatment device according to the embodiment of the present invention.

FIG. 8 is a partial cross-sectional view showing the manipulation part 40 of the energy treatment device 1. As shown in FIG. 8, a rod 34 constituting the transmission part 33 and a plurality of flexural wires 35 (a first flexural wire 36 and a second flexural wire 37) are inserted into the inside of the shaft 32. The transmission part 33 is provided to transmit a driving force for operating a distal portion of the insertion part 2 to the distal portion of the insertion part 2 from the manipulation part 40.

The rod 34 of the transmission part 33 is a rigid rod-shaped member for enabling the first proximal arm 6 and the second proximal arm 21 to swing with respect to the pipe part 31. A distal end of the rod 34 is coupled to the proximal end of the first proximal arm 6 and the proximal end of the second proximal arm 21 by a link. The link disposed at the distal end of the rod 34 converts straight movement of the rod 34 toward the longitudinal axis direction of the shaft 32 into swinging movements of the first proximal arm 6 and the second proximal arm 21. In the present embodiment, when the rod 34 moves to the distal side, the first proximal arm 6 and the second proximal arm 21 swing with respect to the pipe part 31 so that the first proximal arm 6 and the second proximal arm 21 open against the pipe part 31. When the rod 34 moves to a proximal side, the first proximal arm 6 and the second proximal arm 21 swing with respect to the pipe part 31 so that the first proximal arm 6 and the second proximal arm 21 close against the pipe part 31. The proximal end of the rod 34 is coupled to a second grip 52 to be described below of the manipulation part 40. Due to operations of the second grip 52, the rod 34 is operated to advance from and retract into the shaft 32 in the longitudinal axis direction of the shaft 32.

The first flexural wire 36 among the plurality of flexural wires 35 is a flexible linear member for enabling the first distal arm 7 shown in FIG. 2 to swing with respect to the first proximal arm 6. A distal end of the first flexural wire 36 is connected with the first distal arm 7. As shown in FIG. 8, a proximal end of the first flexural wire 36 is fixed to a first slide lever 45 of the manipulation part 40. When the first slide lever 45 moves to the proximal side, the first flexural wire 36 also moves to the proximal side along with the first slide lever 45. When the first flexural wire 36 moves to the proximal side, the distal end of the first distal arm 7 swings toward the second arm 20 side using the swing axis line L2 on which the first distal arm 7 and the first proximal arm 6 are coupled with each other as a center of swing.

The second flexural wire 37 among the plurality of flexural wires 35 is a flexible linear member for enabling the second distal arm 22 to swing with respect to the second proximal arm 21. A distal end of the second flexural wire 37 is connected with the second distal arm 22 shown in FIG. 2. As shown in FIG. 8, a proximal end of the second flexural wire 37 is fixed to a second slide lever 49 of the manipulation part 40. When the second slide lever 49 moves to the proximal side, the second flexural wire 37 also moves to the proximal side along with the second slide lever 49. When the second flexural wire 37 moves to the proximal side, the distal end of the second distal arm 22 swings toward the first arm 5 side using the swing axis line L3 on which the second distal arm 22 and the second proximal arm 21 are coupled with each other as a center of swing.

The outer sheath 38 shown in FIG. 1 is a tubular elastic member of which the diameter of a distal end thereof is decreased. The distal end of the outer sheath 38 has substantially the same opening size as the diameter of the knife wire 11 when an external force is not exerted thereon, and has sufficient elasticity for the outer sheath to be pressed to be widened by the pair of arms 4 and the shaft 32. In the present embodiment, a distal end portion of the outer sheath 38 has a plurality of flap parts 38a and film parts 38b. The plurality of flap parts 38a are formed to be divided by notches that are formed in a plurality of spots in the circumferential direction of the outer sheath 38 along the longitudinal direction of the outer sheath 38. The film parts 38b connect adjacent flap parts 38a with notches interposed therebetween.

As shown in FIGS. 1 and 8, the manipulation part 40 includes a first grip 41, the second grip 52, a coupling shaft 54, and a ratchet part 55. The first grip 41 is fixed to the proximal end of the shaft 32 of the pipe part 31. The second grip 52 is coupled to the proximal end of the rod 34 projecting from the proximal end of the shaft 32 and extending to the proximal side. The coupling shaft 54 couples the first grip 41 with the second grip 52 to cause them to freely pivot. The ratchet part 55 holds the coupling shaft 54 to be in a predetermined positional relationship with the first grip 41 and the second grip 52.

As shown in FIG. 1, the first grip 41 has a handle 42, the connector 43, a first slider part 44 (see FIG. 8), a second slider part 48, and a release lever 56. The handle 42 is formed in a ring shape which enables an operator to hook his or her finger therearound. The connector 43 is configured to be connected to a high-frequency power supply device for applying high-frequency current to the knife wire 11. The first slider part 44 is provided to operate the first distal arm 7 to bend with respect to the first proximal arm 6. The second slider part 48 is provided to operate the second distal arm 22 to bend with respect to the second proximal arm 21. The release lever 56 is a part of the ratchet part 55 and is provided to change engaging states with respect to the second grip 52.

As shown in FIG. 8, a portion of the first grip 41 to which the proximal end of the shaft 32 is fixed has a through-hole in which the rod 34 freely advances and retreats. The proximal end of the rod 34 disposed inside the shaft 32 extends to the second grip 52 via the through-hole of the first grip 41 and then is coupled to the second grip 52.

The first slider part 44 has the first slide lever 45 that can move to advance or retreat in a predetermined first linear direction, and a first guide part 46 which guides the first slide lever 45 in the predetermined first linear direction.

In the present embodiment, the first guide part 46 guides the first slide lever 45 so that the first slide lever 45 moves to advance and retreat in parallel with the direction of the longitudinal axis of the pipe part 31. In addition, as shown in FIG. 8, the first guide part 46 has a first stopper mechanism 47. The first stopper mechanism 47 holds a position of the first slide lever 45 on the first guide part 46 when the first slide lever 45 moves to the most proximal side. In addition, the first slide lever 45 is coupled to the proximal end of the first flexural wire 36 of which the distal end is fixed to the first distal arm 7.

When the first slide lever 45 is positioned on the most distal side of the first guide part 46, the first slide lever is in a linear state with the first distal arm 7 not bending with respect to the first proximal arm 6. When the first slide lever 45 is positioned on the most proximal side of the first guide part 46, the first distal arm 7 is in a bending state in which the first distal arm bends toward the second arm 20 side from the first proximal arm 6.

The second slider part 48 has the second slide lever 49 that can move to advance or retreat in a predetermined second linear direction, and a second guide part 50 which guides the second slide lever 49 in the predetermined second linear direction.

In the present embodiment, the second guide part 50 guides the second slide lever 49 so that the second slide lever 49 moves to advance and retreat in parallel with the direction of the longitudinal axis of the pipe part 31. That is, in the present embodiment, the first slide lever 45 and the second slide lever 49 can advance and retreat along straight lines parallel with each other.

The second guide part 50 has a second stopper mechanism 51. The second stopper mechanism 51 holds a position of the second slide lever 49 on the second guide part 50 when the second slide lever 49 moves to the most proximal side. The second slide lever 49 is coupled to the proximal end of the second flexural wire 37. The distal end of the second flexural wire 37 is fixed to the second distal arm 22.

When the second slide lever 49 is positioned at apposition where is the most distal with respect to the second guide part 50, the second distal arm 22 is in a straight state without bending with respect to the second proximal arm 21. When the second slide lever 49 is positioned at apposition where is the most proximal with respect to the second guide part 50, the second distal arm 22 is in a bending state in which the second distal arm 22 bends toward the first arm 5 with respect to the second proximal arm 21.

The first slide lever 45 can move to advance and retreat along the first guide part 46. The second slide lever 49 can move to advance and retreat along the second guide part 50. The first slide lever 45 and the second slide lever 49 can move to advance and retreat independently of each other.

As shown in FIG. 1, the second grip 52 has a handle 53, and a ratchet teeth part 58. The handle 53 is formed in a ring shape which enables the operator to hook his or her finger therearound. The ratchet teeth part 58 is a part of the ratchet part 55 which engages with the release lever 56 disposed in the first grip 41.

When the handle 53 of the second grip 52 moves close to the handle 42 of the first grip 41, the second grip 52 pivots with respect to the first grip 41, with the coupling shaft 54 as the center of pivoting. Accordingly, the rod 34 of the transmission part 33 moves to the proximal side. In addition, when the handle 53 of the second grip 52 moves away from the handle 42 of the first grip 41, the second grip 52 pivots away from the first grip 41 having the coupling shaft 54 as the center of pivoting, and thereby the rod 34 of the transmission part 33 moves to the distal side. With such pivoting operations of the second grip 52 with respect to the first grip 41, the rod 34 advances from and retreats into the shaft 32, and the first proximal arm 6 and the second proximal arm 21 swing with respect to the shaft 32. That is, the first grip 41 and the second grip 52 constitute an opening-closing manipulation mechanism for manipulating the first arm 5 and the second arm 20 to perform opening-closing operations.

The ratchet part 55 has the release lever 56 disposed in the first grip 41 and the ratchet teeth part 58 disposed in the second grip.

The release lever 56 is provided with a claw part 57 that engages with the ratchet teeth part 58. When the operator operates the release lever 56, engagement states of the claw part 57 with the ratchet teeth part 58 can be switched.

The ratchet teeth part 58 is provided with a plurality of teeth 59 which can engage with the claw part 57 of the release lever 56. When the claw part 57 engages with any of the plurality of teeth 59, a position of the second grip 52 can be fixed with respect to the first grip 41.

Figure 9:
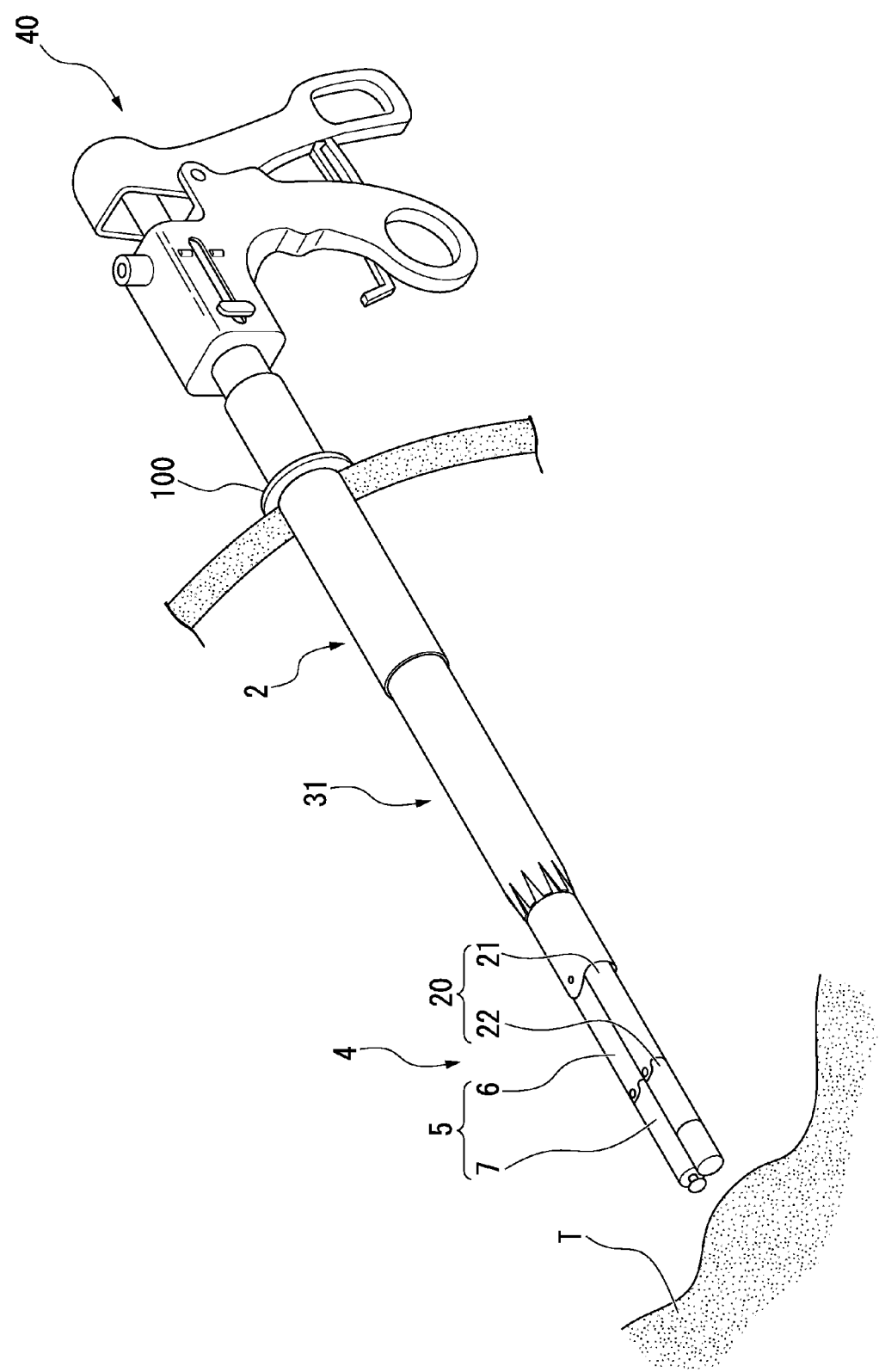
FIG. 9 is a view describing a use method of the energy treatment device according to the embodiment of the present invention.
Figure 10:
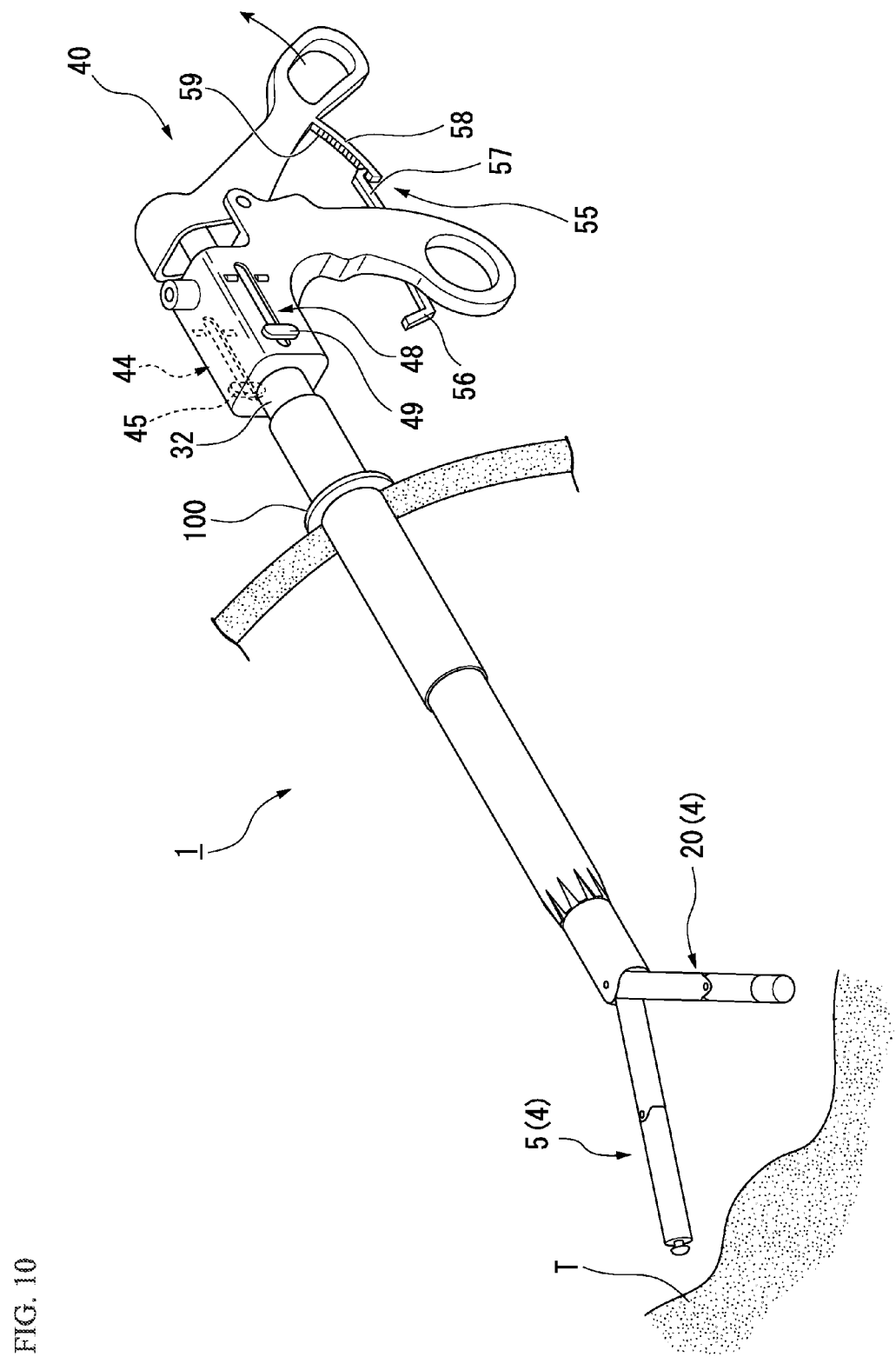
FIG. 10 is a view describing the use method of the energy treatment device according to the embodiment of the present invention.
Figure 11:
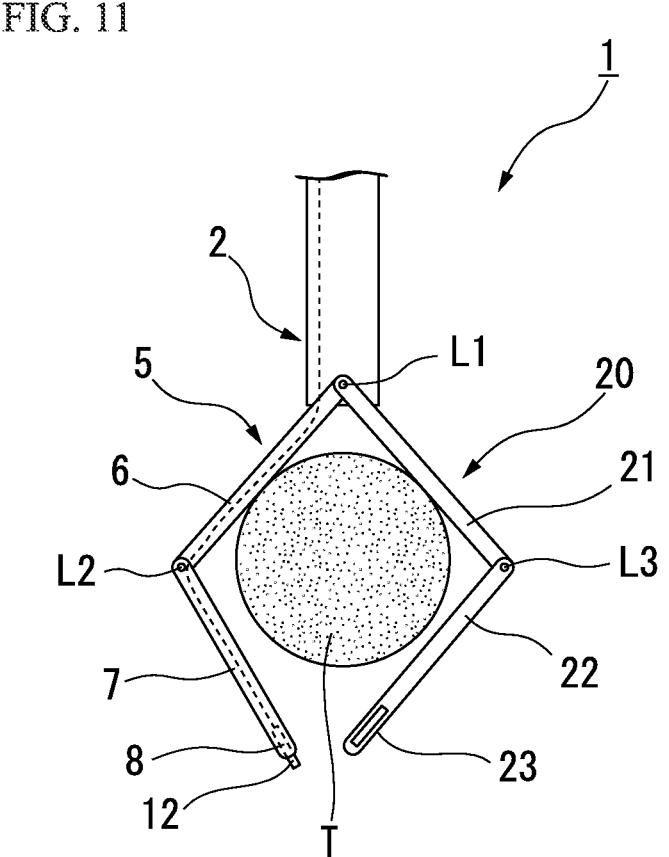
FIG. 11 is a view describing an operation of a distal portion of the energy treatment device when the energy treatment device according to the embodiment of the present invention is used.
Figure 12:
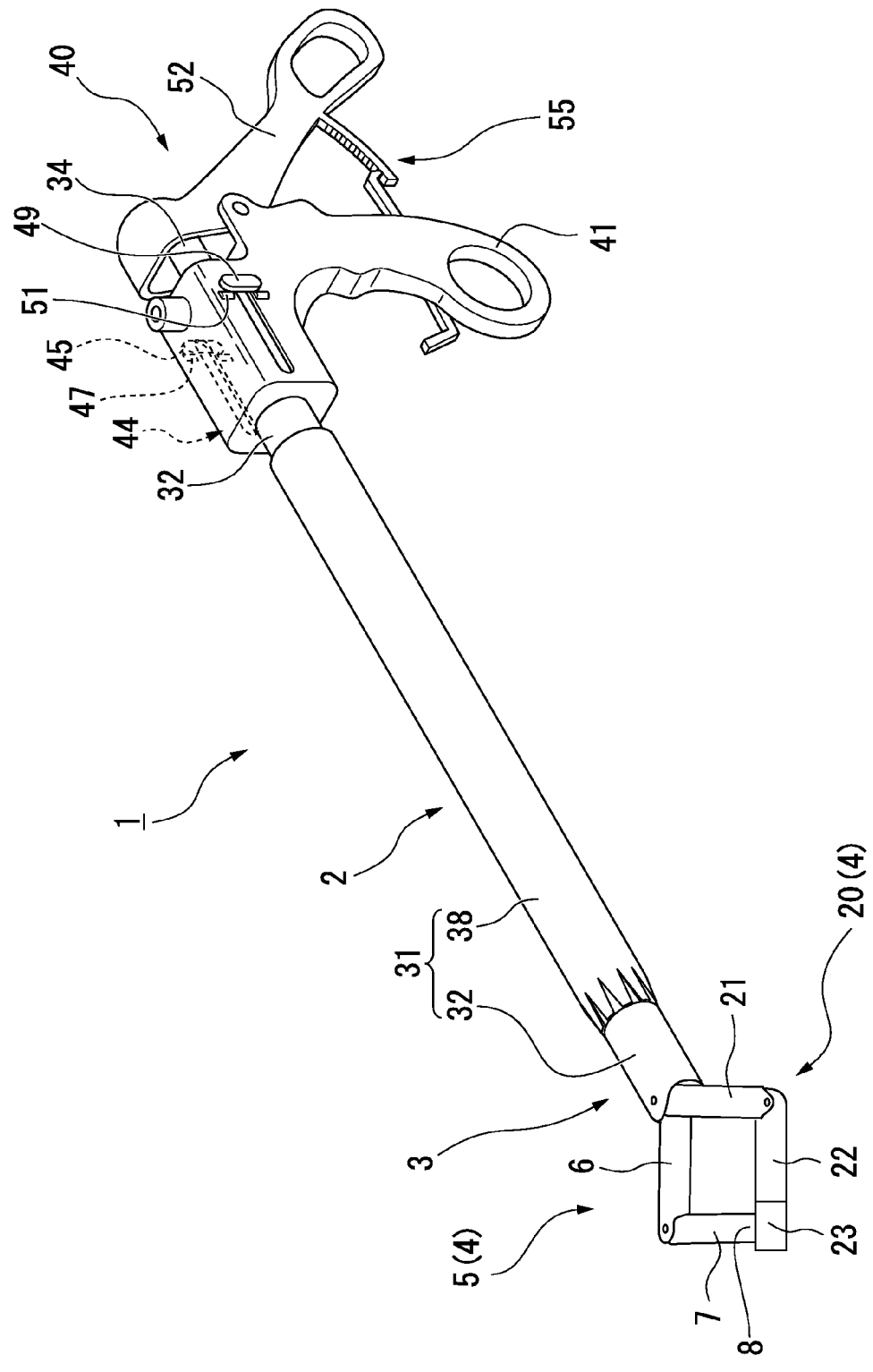
FIG. 12 is view describing the use method of the energy treatment device according to the embodiment of the present invention.
Figure 13:
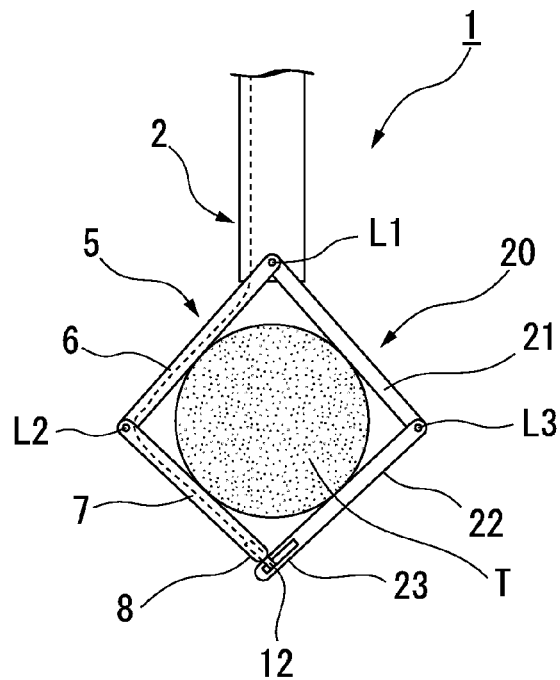
FIG. 13 is a view describing an operation of the distal portion of the energy treatment device when the energy treatment device according to the embodiment of the present invention is used.
Figure 14:
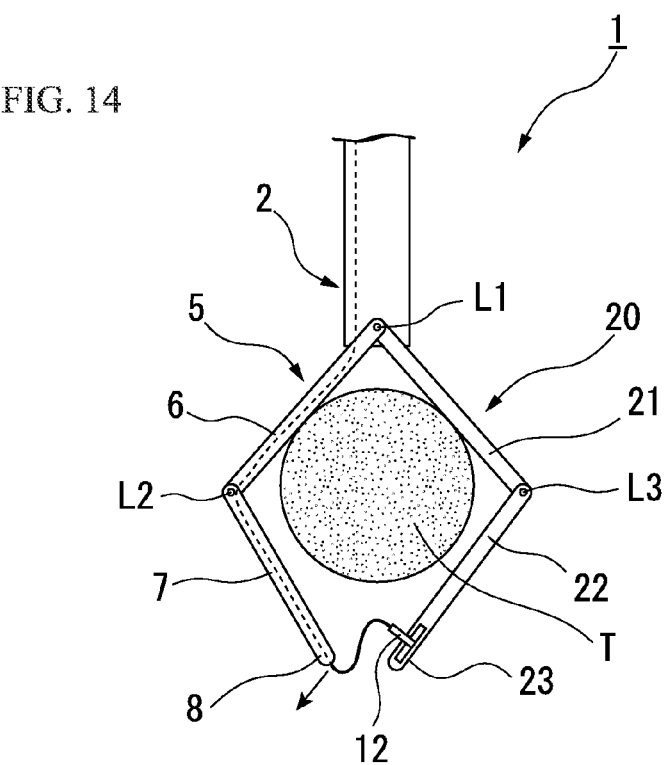
FIG. 14 is a view describing the operation of the distal portion of the energy treatment device when the energy treatment device according to the embodiment of the present invention is used.
Figure 15:
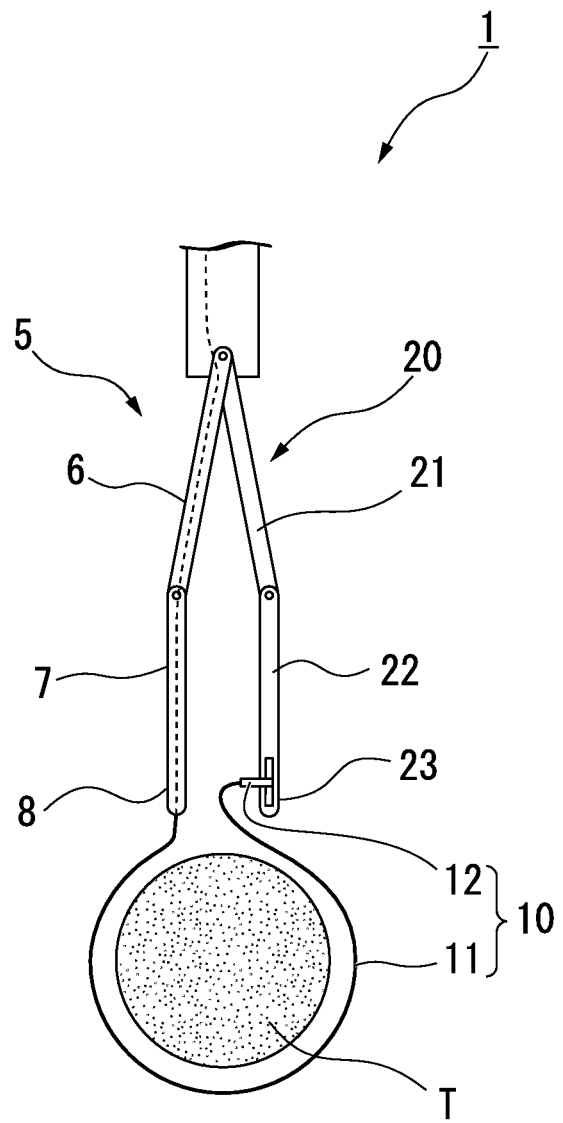
FIG. 15 is a view describing the operation of the distal portion of the energy treatment device when the energy treatment device according to the embodiment of the present invention is used.
Figure 16:
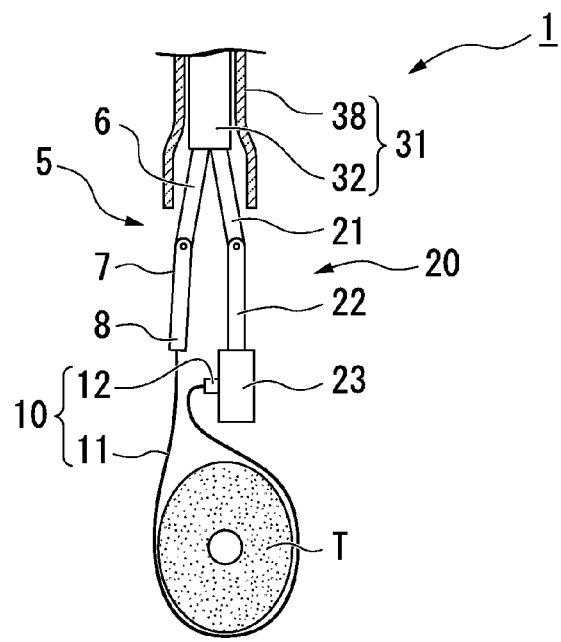
FIG. 16 is a view describing a binding method of an incision target site using the energy treatment device according to the embodiment of the present invention.
Figure 17:
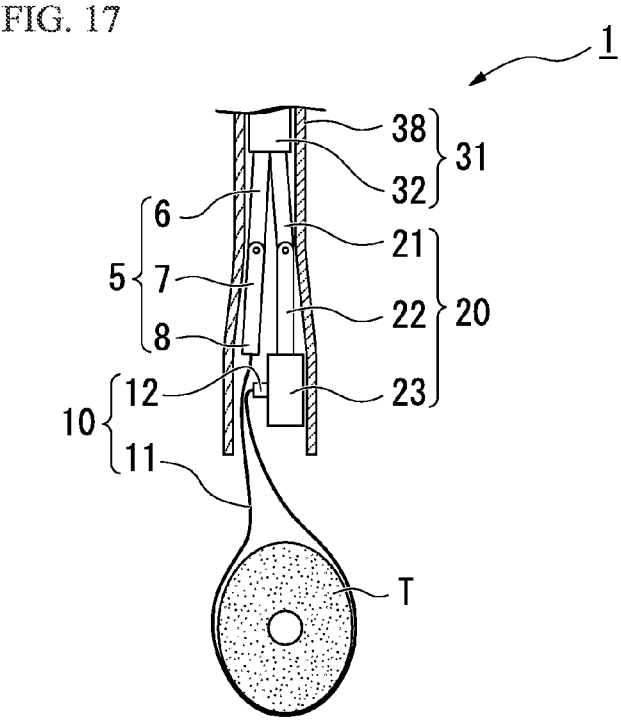
FIG. 17 is a view describing the binding method of the incision target site using the energy treatment device according to the embodiment of the present invention.
Figure 18:
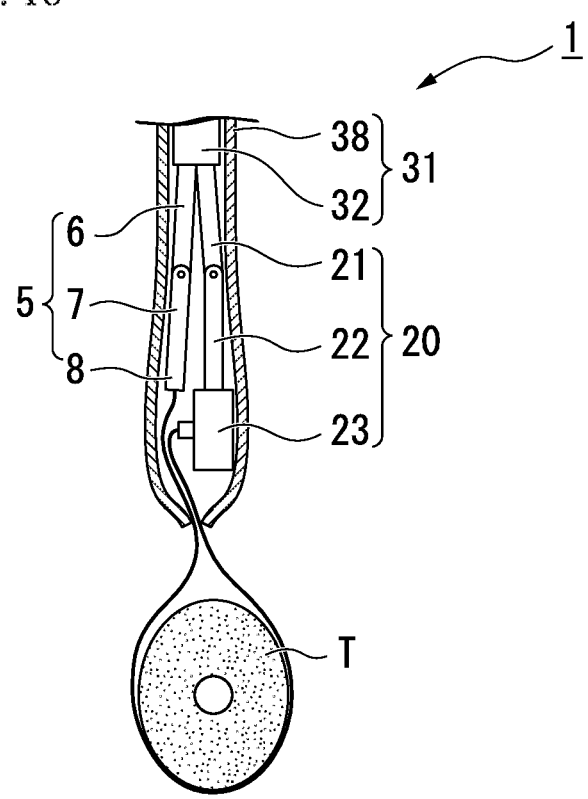
FIG. 18 is a view describing the binding method of the incision target site using the energy treatment device according to the embodiment of the present invention.

Next, an example of a procedure in which the energy treatment device 1 according to the present embodiment is used will be shown. FIGS. 9 and 10 are views describing a use method of the energy treatment device 1. FIG. 11 is a view describing an operation of a distal portion of the energy treatment device 1 when the energy treatment device 1 is used. FIG. 12 is a view describing the use method of the energy treatment device 1. FIGS. 13, 14, and 15 are views describing an operation of the distal portion of the energy treatment device 1 when the energy treatment device 1 is used. FIGS. 16, 17, and 18 are views for describing a binding method of an incision target site using the energy treatment device 1.

The procedure described in the present embodiment a kind of special procedure among laparoscopic procedures. In this laparoscopic procedure, in order to keep positional accuracy, convenience, and time taken for treatment to a suitable level, excision operations, which is for a large target tissue which cannot enter in a loop of a general snare and which are identical to an excision of a pedicle tissue such as a polyp are required.

Specifically, the total laparoscopic hysterectomy (TLH) and laparoscopic supracervical hysterectomy (LSH) using the energy treatment device 1 according to the present embodiment are exemplified.

Both the total laparoscopic hysterectomy and laparoscopic supracervical hysterectomy are hysterectomies, but have a difference in treatment target sites. In the total laparoscopic hysterectomy, after treatment of a plurality of ligaments which support a uterus, blood vessels, adherent tissues, and adnexa is performed, the uterus is separated through a treatment of incising the vaginal canal. In the laparoscopic supracervical hysterectomy, after the treatment of a plurality of ligaments which support a uterus, blood vessels, adherent tissues, and adnexa is performed, the uterus is separated through a treatment of incising the cervix.

The energy treatment device 1 according to the present embodiment is used in procedures in which a vaginal canal or a periphery of a cervix is treated to be incised in order to separate a uterus.

First, in a known procedure, treatment of a plurality of ligaments which support a uterus, blood vessels, adherent tissues, and adnexa is performed. As a result of this procedure, the uterus has a form of a huge polyp in which the vaginal canal or cervix forms a stalk.

Next, as shown in FIG. 9, the distal end (the pair of arms 4) of the energy treatment device 1 according to the present embodiment is guided to an incision target site T (a vaginal canal or cervix) via a trocar 100 deployed on an abdominal wall. Note that a uterus manipulator for adjusting a position of a uterus or the like, grasping forceps, or other devices may be inserted into a body via another trocar when necessary.

When the energy treatment device 1 is inserted into a trocar, the first arm 5 and the second arm 20 are in a linear state in which the arms are parallel with the longitudinal axis of the pipe part 31 and in a form in which the arms are easily inserted into the trocar. That is, when the energy treatment device 1 is inserted into the trocar, the first proximal arm 6 and the first distal arm 7 extend on the same axis and the second proximal arm 21 and the second distal arm 22 extend on the same axis on a straight line that is parallel with the longitudinal axis of the shaft 32 constituting the pipe part 31.

When the first arm 5 and the second arm 20 are in a linear state in which the arms are parallel with the longitudinal axis L4 of the pipe part 31, the first arm 5 and the second arm 20 are inside the contour of a cross-section that is orthogonal to the longitudinal axis L4 of the pipe part 31 and do not jut out to an outer side of the radial direction of the pipe part 31. For this reason, a possibility of the first arm 5 or the second arm 20 coming in contact with an unintended tissue inside a body is kept low.

Next, after the distal end of the energy treatment device 1 reaches near the incision target site T, an operator operates the first slider part 44, the second slider part 48, the first grip 41, and the second grip 52 of the manipulation part 40 as shown in FIG. 10. Through this manipulation, the first arm 5 and the second arm 20 respectively move from the pipe part 31 to make a space that is large enough for the incision target site T to be placed between the first arm 5 and the second arm 20, and thereby the pair of arms 4 are opened.

For example, when the operator manipulates the second grip 52 so that the handle 53 of the second grip 52 is moved away from the handle 42 of the first grip 41, the rod 34 coupled to the second grip 52 moves to the distal side of the shaft 32. When the rod 34 moves to the distal side of the shaft 32, the first proximal arm 6 and the second proximal arm 21 respectively swing to open with respect to the shaft 32. Accordingly, the pair of arms 4 provided in the distal portion of the insertion part 2 are opened.

In addition, the first arm 5 and the second arm 20 are maintained in a plane-symmetric bending state, with the plane which includes the longitudinal axis of the shaft 32 and extends in the direction of the swing axis line of the first proximal arm 6 and the second proximal arm 21 with respect to the shaft 32 as a plane of symmetry. The first slide lever 45 of the first slider part 44 and the second slide lever 49 of the second slider part 48 are moved to the proximal side, and thereby a direction of the first distal arm 7 with respect to the first proximal arm 6 and a direction of the second distal arm 22 with respect to the second proximal arm 21 may be adjusted, when necessary.

Next, the operator moves the distal end portion of the insertion part 2 so that the incision target site T is positioned between the first arm 5 and the second arm 20 as shown in FIG. 11. Further, by causing the first distal arm 7 to bend toward the first proximal arm 6 and then causing the second distal arm 22 to bend toward the second proximal arm 21 as shown in FIGS. 12 and 13, the first distal arm 7 and the second distal arm 22 are operated to bend so that the distal end of the first distal arm 7 approaches the distal end of the second distal arm 22.

That is, the first slide lever 45 is moved to the proximal side and then the second slide lever 49 is moved to the proximal side as shown in FIG. 12. For example, the first slide lever 45 and the second slide lever 49 are moved to the proximal side to the position in which the first slide lever 45 and the second slide lever 49 are respectively in a fixed state due to the first stopper mechanism 47 and the second stopper mechanism 51. As a result, the first arm 5 and the second arm 20 are maintained in a bending state in which the arms can symmetrically rotate 180° about the longitudinal axis of the shaft 32. In addition, at this time, the positional relationship between the first grip 41 and the second grip 52 does not change. In other words, the first grip 41 and the second grip 52 are in a state of being positioned by the ratchet part 55.

The locking member 12 is installed in the first treatment part 8 disposed at the distal end of the first arm 5. The second treatment part 23 is disposed at the distal end of the second arm 20. The locking member 12 is guided into the guide part 25 of the second treatment part 23 as the first distal arm 7 and the second distal arm 22 close (see FIG. 6). Here, a position in which the distal ends of the pair of arms 4 are in proximity to each other so that the locking member 12 of the treatment member 10 is locked in the locked part 24 is referred to as a proximity position. A position in which a distance between the distal ends of the pair of arms 4 is longer than a distance thereof at the proximity position is referred to as a separation position. Movement directions of the respective first arm 5 and second arm 20 are regulated so that the arms perform reciprocating movements having a predetermined track between the proximity position and the separation position. For this reason, the operator can guide the locking member 12 into the guide part 25 by only performing a manipulation to close the pair of arms 4.

Cases in which the first arm 5 and the second arm 20 are pressed by another tissue and warp or are deviated from their positions during the treatment performed inside a body are considered. However, since the guide part 25 has the tapered shape, when the locking member 12 enters the guide part 25, the locking member 12 is guided into the guide part 25 even though positions of the distal end of the first arm 5 and the distal end of the second arm 20 are slightly deviated.

When the locking member 12 reaches inside the guide part 25, the locking member 12 comes in contact with the inner face of the guide part 25. As a result, the first arm 5 and the second arm 20 cannot close any further. Accordingly, the operator of the energy treatment device 1 can recognize that the locking member 12 has properly reached inside the guide part 25. In addition, when the locking member 12 reaches inside the guide part 25, the first arm 5 has been bent in the coupling portion between the first distal arm 7 and the first proximal arm 6, and the second arm 20 has been bent in the coupling portion between the second distal arm 22 and the second proximal arm 21.

For this reason, the incision target site placed between the first arm 5 and the second arm 20 is not pinched by the first arm 5 and the second arm 20, and does not receive a pressing force from another tissue or the like.

When the locking member 12 reaches inside the guide part 25, the operator moves the first distal arm 7 with respect to the first proximal arm 6 in the direction in which the first distal arm 7 is in a linear state with respect to the first proximal arm 6 while keeping the first proximal arm 6 and the second proximal arm 21 in the positional relationship as shown in FIG. 14. Specifically, the first slide lever 45 of the first slider part 44 shown in FIG. 12 is moved to the distal side. At this time, the first grip 41 and the second grip 52 may be in a state of being positioned by the ratchet part 55. By holding the positions of the first grip 41 and the second grip 52 with the ratchet part 55, a possibility of the first proximal arm 6 and the second proximal arm 21 inadvertently moving during the manipulation of the first slide lever 45 can be kept low. In addition, it is not necessary to exert a force on the first grip 41 and the second grip 52 to hold the positions of the first grip 41 and the second grip 52.

When the first distal arm 7 is moved in the direction in which the first distal arm 7 is in the linear state with respect to the first proximal arm 6, the first treatment part 8 provided at the distal end of the first distal arm 7 turns about the swing axis line L2 on which the first distal arm 7 is coupled to the first proximal arm 6. Further, as the first treatment part 8 is operated to turn from the first distal arm 7, the locking member 12 is moved to the distal side of the second treatment part 23. In other words, the locking member 12 disposed inside the guide part 25 enters the first slit part 26, passes over the projecting part 28, and then reaches the engaging part 27. Accordingly, the locking member 12 is electrically connected with the contact point part 29 in the engaging part 27, and is held by the engaging part 27 due to the action of the projecting part 28.

Next, the operator opens the first proximal arm 6 and the second proximal arm 21 and separates the distal end of the first arm 5 from the distal end of the second arm 20 as shown in FIGS. 14 and 15. Then, the locking member 12 is released from the opening which has held the locking member 12 in the first treatment part 8, and the locking member 12 is held only in the engaging part 27 of the second treatment part 23. In other words, when the first proximal arm 6 and the second proximal arm 21 open and the distal end of the first arm 5 is separated from the distal end of the second arm 20, the treatment member 10 is transferred from the first arm 5 to the second arm 20. Specifically, in the present embodiment, when the first proximal arm 6 and the second proximal arm 21 open and the distal end of the first arm 5 is separated from the distal end of the second arm 20, the locking member 12 is transferred from the first treatment part 8 to the second treatment part 23. The knife wire 11 is drawn out from the opening 8b (see FIG. 4) of the first treatment part 8. Further, as the operator moves the entire energy treatment device 1 to the proximal side while bringing the knife wire 11 in contact with the incision target site T, the knife wire 11 is placed along the outer circumference of the incision target site T. In this state, the incision target site T is in a state in which almost half of the circumference on the distal side relative to the energy treatment device 1 is surrounded by the knife wire 11 as shown in FIG. 15.

In the state in which the incision target site T is surrounded by the knife wire 11, the operator undoes the bending state of the first distal arm 7 and the first proximal arm 6, undoes the bending state of the second distal arm 22 and the second proximal arm 21, and further closes the first proximal arm 6 and the second proximal arm 21 as shown in FIG. 16. Accordingly, the pair of arms 4 are in the same linear state at the time of insertion of the energy treatment device 1 into the body. Furthermore, the operator moves the outer sheath 38 of the pipe part 31 to the distal side of the shaft 32 of the pipe part 31 as shown in FIGS. 17 and 18. Then, the distal end of the outer sheath 38 moves to the distal side relative to the pair of arms 4 to place the pair of arms 4 together and cover the outer side of the arms, goes beyond the first treatment part 8 and the second treatment part 23, and then the diameter of the outer sheath 38 decreases due to its own restoring force. As the diameter of the distal end of the outer sheath 38 decreases, the opening at the distal end of the outer sheath 38 holds the knife wire 11 in a joining state.

The operator further moves the position of the opening of the distal end of the outer sheath 38 on the distal side to bind the incision target site T using the knife wire 11.

By applying a high-frequency current to the knife wire 11 while the knife wire 11 binds the incision target site T, the incision target site T is resected. When the incision target site T has been excised, the energy treatment device 1 is taken out of the body, and thereby the excision treatment is completed. Note that, for the purpose of preventing the knife wire 11 from entangling when the energy treatment device 1 is taken out of the body, a portion of the knife wire 11 exposed inside the body after resection may be accommodated in the outer sheath 38.

The energy treatment device 1 according to the present embodiment is configured such that, through opening-closing operations of the first arm 5 and the second arm 20 performed using their respective axis lines provided at the distal end of the pipe part 31 as the center of swing, the first treatment part 8 and the second treatment part 23 perform respective movements between the state in which the first treatment part 8 and the second treatment part 23 are separated from each other and the state in which the first treatment part 8 and the second treatment part 23 are in proximity, and in the state in which the first treatment part 8 and the second treatment part 23 are in closest proximity, the locking member 12 installed in the first treatment part 8 engages with the engaging part 27 of the second treatment part 23.

In other words, movement routes of the first treatment part 8 and the second treatment part 23 are respectively regulated. Thus, when the first arm 5 and the second arm 20 are merely closed by the operator, the first treatment part 8 of the first arm 5 and the second treatment part 23 of the second arm 20 are in the positional relationship in which the knife wire 11 can be transferred. In this manner, manipulations to move the first treatment part 8 and manipulations to move the second treatment part 23 are interlinked as automatically coordinated manipulations. Therefore, if the operator arranges an excision line between the first arm 5 and the second arm 20 so that the excision line is surrounded by the first arm 5 and the second arm 20 in their opening state and manipulates the manipulation part 40 to close the first arm 5 and the second arm 20, the knife wire 11 can be transferred while the operator is unaware of a coordinated manipulation. In addition, the energy treatment device 1 according to the present embodiment can perform transfer of the knife wire 11 even when the first treatment part 8 and the second treatment part 23 are in a position in which the transfer state of the knife wire 11 is difficult to be checked with laparoscopic images.

Furthermore, even when the energy treatment device 1 approaches the excision line in a direction oblique with respect to the excision line on which a uterus is severed, the knife wire 11 can have its diameter decreased in a state in which the knife wire is placed along the excision line as the knife wire 11 is placed around the outer surface of the incision target site on the excision line positioned on the distal side of the energy treatment device and binds the incision target site. For this reason, the energy treatment device 1 according to the present embodiment can perform an excision treatment along an excision line with accuracy, ease, and speed in comparison to cases in which excision is performed using a needle electrode or incision forceps.

Modified Example 1

Figure 19:
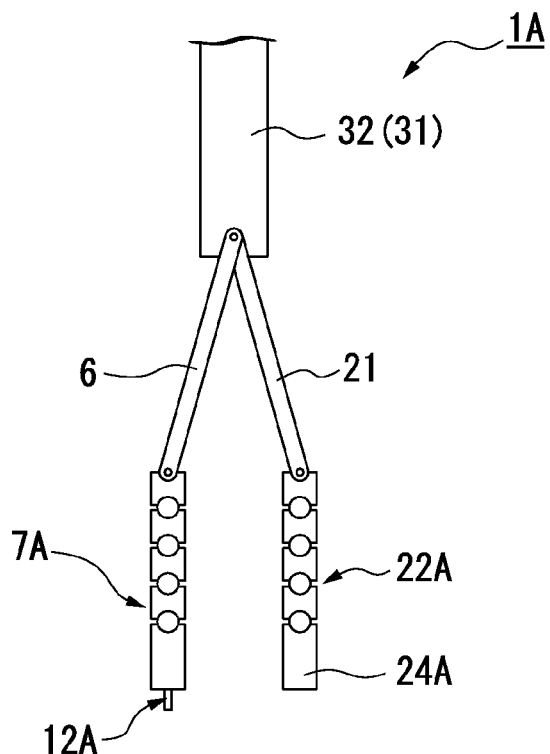
FIG. 19 is a plan view showing a configuration of a modified example of an energy treatment device according to the embodiment of the present invention.
Figure 20:
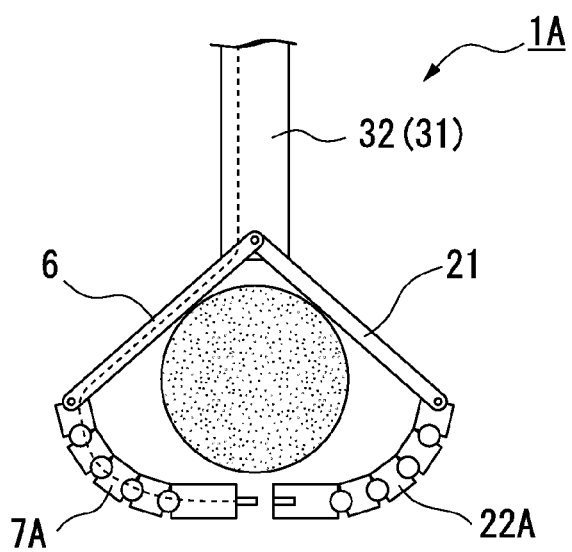
FIG. 20 is a view describing an operation during use of the energy treatment device of the modified example according to the embodiment of the present invention.
Figure 21:
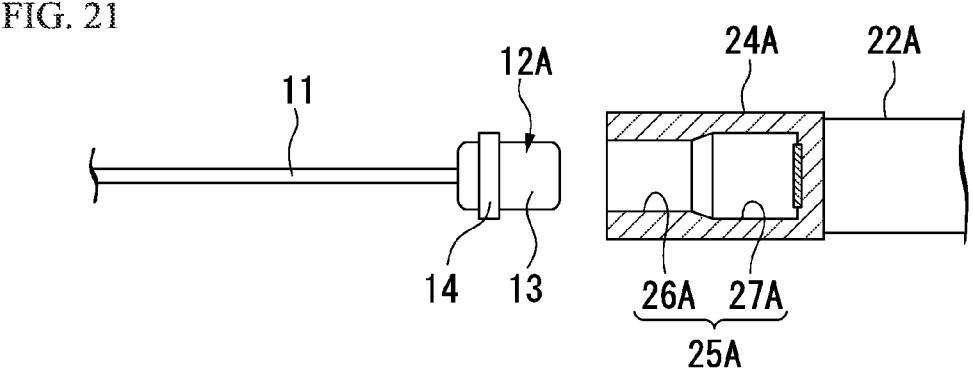
FIG. 21 is a schematic partial cross-sectional view describing a configuration of a second treatment part of the energy treatment device according to the embodiment of the present invention.
Figure 22:
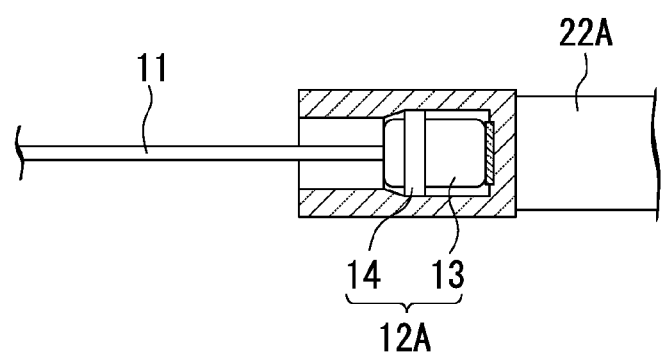
FIG. 22 is a schematic partial cross-sectional view describing the configuration of the second treatment part of the energy treatment device according to the embodiment of the present invention.

An energy treatment device 1A according to a modified example of the present embodiment will be described. FIG. 19 is a plan view showing a configuration of the modified example of the energy treatment device 1A. FIG. 20 is a view describing an operation during use of the energy treatment device 1A of the present modified example. FIG. 21 is a schematic partial cross-sectional view describing a configuration of a second treatment part of the energy treatment device 1A. FIG. 22 is a schematic partial cross-sectional view describing the configuration of the second treatment part of the energy treatment device 1A.

As shown in FIG. 19, the energy treatment device 1A of the present modified example has a first distal arm 7A and a second distal arm 22A, which have different structures from the first distal arm 7 and the second distal arm 22, instead of the first distal arm 7 and the second distal arm 22.

The first distal arm 7A has a structure in which a plurality of tubular curving parts or joint rings (which are referred to hereinafter as joint rings etc.) are bendably coupled with each other and has a structure in which the arm can be curved as a whole. In the first distal arm 7A of the present modified example, the joint rings are all turnably coupled with each other having turning axes parallel with each other. For this reason, the first distal arm 7A performs curving operations on the plane perpendicular to each of the turning axes.

The second distal arm 22A has a structure in which a plurality of tubular curving parts or joint rings (which are referred to hereinafter as joint rings or the like.) are bendably coupled with each other like the first distal arm 7A. The second distal arm 22A is configured to be capable of being curved as a whole with the above-described structure. In the second distal arm 22A of the present modified example, each of the joint rings or the like has respective rotation axis. All of the rotation axes are parallel to each other. All of the joint rings or the like are rotatably coupled with each other. For this reason, the second distal arm 22A performs curving operations on a plane perpendicular to each of the rotation axis. The rotation axes of the second distal arm 22A are parallel with each turning axis of the first distal arm 7A. For this reason, the second distal arm 22A performs curving operations along a plane parallel with the first distal arm 7A. In the present modified example, the first distal arm 7A and the second distal arm 22A perform curving operations on the same plane.

Furthermore, as shown in FIGS. 21 and 22, the energy treatment device 1A of the present modified example has a locking member 12A provided instead of the locking member 12 of the treatment member 10 and a locked part 24A provided instead of the locked part 24 of the second treatment part 23.

The locking member 12A has a rigid part 13 and an elastic part 14. The rigid part 13 is shaped like a stick that is long in a direction in which the longitudinal axis of the knife wire 11 extends to the distal side. The elastic part 14 is disposed on the outer circumferential surface of the rigid part 13.

The locked part 24A has a hole part 25A into which the locking member 12A is inserted. The hole part 25A is a portion of the second treatment part 23 in which an introducing part 26A and a containing part 27A are formed. The introducing part 26A has internal dimensions slightly larger than the rigid part of the locking member 12A. The containing part 27A is connected with the introducing part 26A and is formed with internal dimensions larger than the introducing part 26A.

The containing part 27A of the locked part 24A contains a part of or the entire locking member 12A. At this time, the elastic part 14 is restored in the containing part 27A due to elasticity of the elastic part 14 so that the elastic part has larger internal dimensions than the introducing part 26A.

In the present modified example, curved states of the first distal arm 7A and the second distal arm 22A can be adjusted using the manipulation part 40 so that the distal end of the first distal arm 7A and the distal end of the second distal arm 22A come in proximity with each other and thus the locking member 12A can be transferred as in the above-described embodiment.

The energy treatment device 1A of the present modified example can bind an incision target site by placing the knife wire 11 around the incision target site as does the energy treatment device 1 of the above-described embodiment, and thereby the incision target site can be severed.

In the present modified example, when the first arm 5 and the second arm 20 are operated to close, the locking member 12A is pushed into the hole part 25A of the locked part 24A. Then, when the locking member 12A is pushed into the hole part 25A of the locked part 24A, the elastic part 14 is stuck in the boundary of the containing part 27A and the introducing part 26A of the locked part 24A, and thereby the locking member 12A is locked so as not to exit the hole part 25A. Therefore, also in the present modified example, the locking member 12A can be transferred from the first arm 5 to the second arm 20 as in the above-described embodiment.

Figure 23:
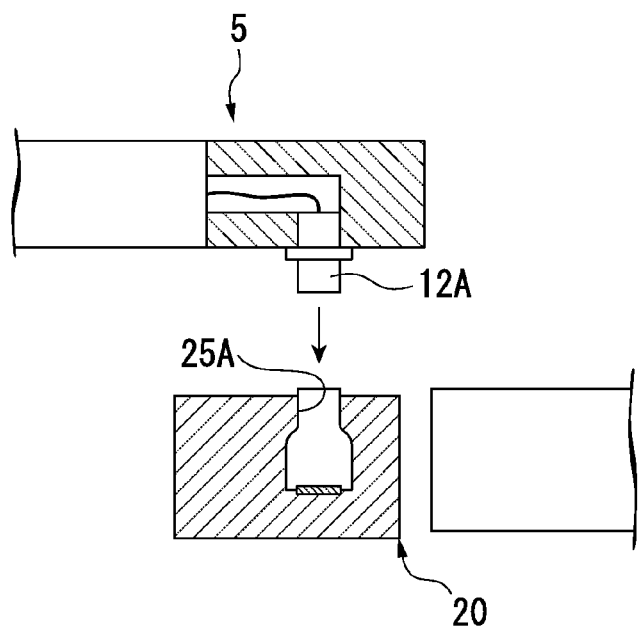
FIG. 23 is a partial cross-sectional view describing a configuration of another modified example of the energy treatment device according to the embodiment of the present invention.

The direction in which the locking member 12A is pushed into the hole part 25A is the direction in which the distal end of the first arm 5 moves. For example, the direction in which the locking member 12A is pushed into the hole part 25A may be a pushing direction in which the distal end of the first arm 5 and the distal end of the second arm 20 abut each other as shown in FIG. 20. In addition, for example, the direction in which the locking member 12A is pushed into the hole part 25A may be a pushing direction in which a side of the distal end of the first arm 5 and a side of the distal end of the second arm 20 are pressed against each other as shown in FIG. 23. In both methods, the locking member 12A can be transferred from the first arm 5 to the second arm 20.

Although the example in which the swing axis line L1 between the first proximal arm 6 and the pipe part 31 and the swing axis line L1 between the second proximal arm 21 and the pipe part 31 are the same axis is shown in the above-described embodiment, the swing axis line L1 between the first proximal arm 6 and the pipe part 31 and the swing axis line L1 between the second proximal arm 21 and the pipe part 31 may not be the same axis and may be parallel with each other.

Although the contact point part 29 is shaped to have the curved face projecting toward the first slit part 26 side in the above-described embodiment, the external shape of the contact point part 29 may resemble the external shape of the locking member 12.

Although the swing axis line L1 is configured to be orthogonal to the longitudinal axis L4 of the pipe part 31 in the above-described embodiment, the swing axis line L1 may be inclined to the longitudinal axis L4 of the pipe part 31.

A shape of the locking member 12 is not limited to the shape in the above-described embodiment. For example, the locking member 12 may have a disc shape fixed to the distal end of the knife wire 11. In addition, the locking member 12 may be disposed in a position deviated from the distal end of the knife wire 11 slightly to the proximal side. For example, the locking member 12 may be formed in a circular shape having a through-hole through which the knife wire 11 can pass and thus the knife wire 11 may be fixed to the locking member 12 in a state in which the knife wire 11 is inserted into the through-hole.

A shape of the locking member 12 may be considered to prevent the locking member from being stuck when the locking member 12 is inserted into the locked part 24. For example, the locking member may have a tapered shape in which the diameter of the member gradually decreases toward the distal side of the knife wire 11. In addition, the locking member may have a spherical shape fixed to a distal portion of the knife wire 11. When the locking member 12 has an inclined surface or a curved surface as in the tapered shape or spherical shape, the locking member 12 seldom collides with the rim of the slit of the locked part 24 and thus the locking member 12 can be smoothly guided inside the locked part 24.

At least outer surfaces of the pair of arms 4 of the above-described embodiment may have an insulating property and the pair of arms 4 may be formed of an insulating material.

Although the tapered shape of the guide part 25 is set to be an inclined plane which becomes wider toward the opening part in the above-described embodiment, the tapered shape of the guide part may be a plane or a curved face.

So far, the respective embodiments of the present invention have been described; however, the technical scope of the present invention is not limited to the embodiments, and combinations of the constituent elements of the embodiments can be changed, or the constituent elements can be variously modified or removed within the scope not deviating from the gist of the present invention. The present invention is not limited by the description provided above, and is limited only by the range of the attached claims.

The invention claimed is:

1. An energy treatment device comprising:
an insertion part which is capable of being inserted into a body;
a pair of arms which has a first arm and a second arm, the first arm and the second arm being provided in a distal portion of the insertion part and being capable of performing an opening-closing operation;
a treatment member which is attachably and detachably provided in the first arm and which performs treatment on a treatment target site;
a locked part which is provided in the second arm and which is capable of locking the treatment member; and
a manipulation part which causes the pair of arms to perform an opening-closing operation,
wherein:
the treatment member includes:
a knife wire configured to have conductivity and to incise a biological tissue using electrical energy; and
a locking member which is positioned with respect to the first arm, being attachable to and detachable from the first arm and capable of being locked by the locked part,
the locked part has a retainer which is capable of holding the locking member with a force stronger than a force of the first arm to hold the locking member,
the insertion part has a shaft to which each of the first arm and the second arm is connected so as to be swingable about a same or parallel axis lines respectively,
the first arm includes:
a first proximal arm which is coupled to a distal end part of the shaft and which swings with respect to the shaft between a state in which the first proximal arm extends in a first direction parallel with a longitudinal axis of the shaft and a state in which the first proximal arm inclines to the longitudinal axis and extends in a second direction radially outward from the shaft; and
a first distal arm which is coupled to the first proximal arm and which swings with respect to the first proximal arm between a state in which the first distal arm extends in the first direction or the second direction in which the first proximal arm extends and a state in which the first distal arm inclines relative to the second direction in which the first proximal arm extends, and
in operation, after the first arm and the second arm are moved to a position in which the first arm and the second arm are in proximity to each other by the opening-closing operation, the locking member held by the first arm is held by the retainer, and the locking member detaches from the first arm while the locking member is held by the retainer of the second arm through an operation in which the first arm and the second arm are separated from each other.

2. The energy treatment device according to claim 1, the second arm comprising:
a second proximal arm which is coupled to the distal end part of the shaft and which swings with respect to the shaft between a state in which the second proximal arm extends in the first direction parallel with the longitudinal axis of the shaft and a state in which the second proximal arm inclines to the longitudinal axis and extends in the second direction radially outward from the shaft; and
a second distal arm which is coupled to the second proximal arm and which swings with respect to the second proximal arm between a state in which the second distal arm extends in the first direction or the second direction in which the second proximal arm extends and a state in which the second distal arm inclines relative to the second direction in which the second proximal arm extends.

3. The energy treatment device according to claim 2, the manipulation part comprising:
a first stopper mechanism which maintains a bending state of the first distal arm with respect to the first proximal arm;

a second stopper mechanism which maintains a bending state of the second distal arm with respect to the second proximal arm; and a first grip and a second grip that causes the pair of arms to perform an opening-closing operation by causing the first proximal arm and the second proximal arm to swing with respect to the shaft while maintaining a state in which the first proximal arm and the second proximal arm have an equal inclination angle with respect to the longitudinal axis of the shaft.

4. The energy treatment device according to claim 3, the second arm further comprising:

a guide part into which the locking member is capable of being inserted and which has a slit part that serves as the retainer; and an engaging part which is disposed on a distal side of the guide part, communicating with the guide part, and being capable of engaging with the locking member, and wherein, when the first arm moves the locking member to a distal side of the second arm from the guide part, the locking member engages with the engaging part.

5. The energy treatment device according to claim 4, wherein:

the locking member has conductivity and is electrically and mechanically connected to the knife wire, the engaging part has a contact point part that is electrically connected with the locking member when the locking member engages with the engaging part, the manipulation part includes:

a connector which is capable of being connected to a high-frequency power supply device that is capable of supplying a high-frequency current;

a first connection part which electrically connects the connector and the knife wire; and a second connection part which electrically connects the connector and the contact point part, and the high-frequency current supplied via the connector is applied to the knife wire when the contact point part is electrically connected with the locking member in the engaging part.

6. The energy treatment device according to claim 2, wherein at least one of the first distal arm and the second distal arm is configured to perform a curving operation.

* * * * *